United States Patent
Akiyama

(10) Patent No.: US 10,830,723 B2
(45) Date of Patent: Nov. 10, 2020

(54) GAS SENSOR AND GAS SENSOR ARRAY

(71) Applicant: KAKE EDUCATIONAL INSTITUTION, Okayama (JP)

(72) Inventor: Norio Akiyama, Okayama (JP)

(73) Assignee: KAKE EDUCATIONAL INSTITUTION, Okayama (JP)

( * ) Notice: Subject to any disclaimer, the term of this patent is extended or adjusted under 35 U.S.C. 154(b) by 641 days.

(21) Appl. No.: 15/323,183

(22) PCT Filed: Jul. 3, 2015

(86) PCT No.: PCT/JP2015/069323
§ 371 (c)(1),
(2) Date: Dec. 30, 2016

(87) PCT Pub. No.: WO2016/002944
PCT Pub. Date: Jan. 7, 2016

(65) Prior Publication Data
US 2017/0138879 A1   May 18, 2017

(30) Foreign Application Priority Data
Jul. 4, 2014 (JP) .................. 2014-139118

(51) Int. Cl.
*G01N 27/12* (2006.01)
*G01N 33/00* (2006.01)
(Continued)

(52) U.S. Cl.
CPC ....... *G01N 27/129* (2013.01); *G01N 33/0031* (2013.01); *H01L 31/0272* (2013.01);
(Continued)

(58) Field of Classification Search
CPC ............. G01N 27/129; G01N 33/0031; H01L 31/108; H01L 31/035227; H01L 31/022466; H01L 31/0272
See application file for complete search history.

(56) References Cited

U.S. PATENT DOCUMENTS

2012/0266658 A1\* 10/2012 Akiyama ............. G01N 27/125
 73/31.05
2013/0122279 A1\* 5/2013 Tsujimoto ................ H01B 1/20
 428/315.7
2015/0308972 A1   10/2015 Akiyama

FOREIGN PATENT DOCUMENTS

EP             1314977 A1    5/2003
JP        2000-058942 A     2/2000
(Continued)

OTHER PUBLICATIONS

Peng et al. Sensors and Actuators B: Chemical 160 (2011) 39-45.\*
(Continued)

*Primary Examiner* — Sally A Merkling
(74) *Attorney, Agent, or Firm* — Leydig, Voit & Mayer, Ltd.

(57) ABSTRACT

A gas sensor containing counter electrodes and a semiconductor nanowire 4 disposed between the counter electrodes 2, 3, wherein the semiconductor nanowire 4 is in a state where light can be irradiated, which sensor measures changes in the electric current associated with adsorption of a gas to the semiconductor nanowire 4, wherein the electric current is generated by irradiation of light on the semiconductor nanowire with a voltage applied to the counter electrodes 2, 3.

18 Claims, 16 Drawing Sheets

(51) Int. Cl.
*H01L 31/0224* (2006.01)
*H01L 31/0272* (2006.01)
*H01L 31/0352* (2006.01)
*H01L 31/108* (2006.01)

(52) U.S. Cl.
CPC ............ *H01L 31/022466* (2013.01); *H01L 31/035227* (2013.01); *H01L 31/108* (2013.01)

(56) References Cited

FOREIGN PATENT DOCUMENTS

| JP | 2002-071638 A | 3/2002 |
|---|---|---|
| JP | 2008-051786 A | 3/2008 |
| JP | 5120904 B2 | 1/2013 |
| WO | WO 2011/055751 A1 | 5/2011 |
| WO | WO 2014/034935 A1 | 3/2014 |

OTHER PUBLICATIONS

Peng et al.(Sensors and Actuators B (160) (2011)39-45) (Year: 2011).*

Akiyama, "Low-Power Sensor for Analyzing Gas Components at Room Temperature," *Chemical Engineering*, 59(3): 241-251 (2014).

Liao et al., "Temperature Dependence of Photoelectrical Properties of Single Selenium Nanowires," *Nanoscale Res. Lett.*, 5(6): 926-929 (2010).

Peng et al., "Improvement of formaldehyde sensitivity of ZnO nanorods by modifying with $Ru(dcbpy)_2(NCS)_2$," *Sensors and Actuators B: Chemical*, 160: 39-45 (2011).

Qin et al., "Rapid photoresponse of single-crystalline selenium nanobelts," *Solid State Communications*, 148: 145-147 (2008).

Sivalingam et al., "Gas-Sensitive Photoconductivity of Porphyrin-Functionalized ZnO Nanorods," *J. Phys. Chem. C*, 116(16): 9151-9157 (2012).

Wu et al., "Soluble Polymer-Based, Blown Bubble Assembly of Single- and Double-Layer Nanowires with Shape Control," *ACS NANO*, 8(4): 3522-3530 (2014).

Japanese Patent Office, International Preliminary Report on Patentability in International Patent Application No. PCT/JP2015/069323 (dated Jan. 14, 2016).

Japanese Patent Office, International Search Report in International Patent Application No. PCT/JP2015/069323 (dated Sep. 1, 2015).

* cited by examiner (a)

(b)

GAS SENSOR AND GAS SENSOR ARRAY

CROSS-REFERENCE TO RELATED APPLICATIONS

This patent application is the U.S. national phase of International Patent Application No. PCT/JP2015/069323, filed on Jul. 3, 2015, which claims the benefit of Japanese Patent Application No. 2014-139118, filed on Jul. 4, 2014, the disclosures of which are incorporated herein by reference in their entireties for all purposes.

TECHNICAL FIELD

The present invention relates to a compact and highly sensitive gas sensor utilizing a photoelectric current generated in semiconductor nanowires, and a compact and highly sensitive gas sensor array with gas analysis capability (in particular, ability to analyze components of mixed gas).

BACKGROUND ART

Gas detection has been used as a danger avoidance technique in gas generation sites such as environmental pollutants and harmful gases. However, the demand therefor is spreading in various fields today such as non-contact diagnosis and health management using oral gas in the medical field, malodor detection in the elderly home and hospital facilities, sensors for mounting robots, sensors for energy harvesting, and the like. Due to the spreading demand for such gas detection, a highly sensitive and compact sensor which can be used repeatedly and further has a gas type analysis function is required.

As a gas sensor which does not require heating and operates at room temperature, the inventor of the present application has proposed a sensor using a selenium nanowire (patent document 1) and a single array type sensor capable of analyzing mixed gas components (patent document 2)

On the other hand, a gas sensor for halogen gas, oxygen molecule or water molecule utilizing a pure boron nanobelt is known as a gas sensor utilizing a photoelectric current of nanomaterials (Patent Document 3). As a proposal utilizing photoconductive phenomenon for gas detection other than nanomaterials, a method of detecting oxygen concentration and humidity change by using the effect of gas atmosphere on the photoelectric current multiplication of the copper phthalocyanine thin film and the metal electrode interface is known (patent document 4). In addition, research reports on photoelectric current relating to nanomaterials include the measurement of photoelectric current in selenium nano-belt (non-patent document 1) and temperature dependency of photoelectric current of selenium nanowire (hereinafter to be also abbreviated as "SeNW") (non-patent document 2). However, there is no report on the utilization of a selenium photoelectric current for a gas sensor.

DOCUMENT LIST

Patent Documents patent document 1: JP-B-5120904
patent document 2: WO 2014/034935
patent document 3: JP-A-2008-51786
patent document 4: JP-A-2002-71638

Non-Patent Document non-patent document 1: Aimiao Qin, Zhou Li, Rusen Yang, et al., Solid State Communications 148 (2008) pp. 145-147. "Rapid photoresponse of single-crystalline selenium nanobelts" non-patent document 2: Zhi-Min Liao, Chong Hou, Li-Ping Liu, et al., Nanoscale Reserch Lett. 5 (2010) pp. 926-929. "Temperature Dependence of Photoelectrical Properties of Single Selenium Nanowires"

SUMMARY OF THE INVENTION

Problems to be Solved by the Invention

In view of the spread of gas detection for various demands, the gas sensor is required to have higher sensitivity, higher responsiveness, and the like. Accordingly, it is an object of the present invention to provide a gas sensor which operates at room temperature, can be used repeatedly and shows sufficiently high sensitivity (preferably, sufficiently high sensitivity and responsiveness). Another object of the present invention is to provide a gas sensor which operates at room temperature, can be used repeatedly, and can analyze gas species with high sensitivity.

Means of Solving the Problems

When a substance is irradiated with a light having energy higher than the band gap thereof, a photoelectric current is generated near the surface. On the other hand, a gas adsorbs to the surface of a substance and injects electrons (positive holes) it has into the substance. Therefore, a dramatic improvement in the sensor sensitivity is expected in semiconductor nanowires, if electrons (positive holes) injected from a gas and photoelectric current carriers near the surface can be efficiently encountered and neutralized by gas adsorption.

In the conventional gas sensor using selenium nanowires as described in patent documents 1 and 2, the present inventors irradiated, on a selenium nanowire, light having energy not less than the band gap of the selenium nanowire. However, it was found that the photoelectric current was buried in the dark current and gas detection was not possible.

Therefore, to generate a photoelectric current in which a clear electric current change accompanying the contact of a gas with the selenium nanowire appears, (1) an element structure with a smaller dark current compared to the photoelectric current, (2) optimization of the device structure to afford highly efficient contact between injected electrons (positive holes) from gas and carrier in the photoelectric current, and (3) optimization of the intensity of the electric field between the counter electrodes were found to be important. Further studies have been made based on such findings, which resulted in the completion of the present invention.

That is, the present invention relates to
[1] a gas sensor comprising counter electrodes and a semiconductor nanowire disposed between the counter electrodes, wherein the semiconductor nanowire is in a state where light can be irradiated, which sensor measures changes in the electric current associated with adsorption of a gas to the semiconductor nanowire, wherein the electric current is generated by irradiation of light on the semiconductor nanowire with a voltage applied to the counter electrodes,
[2] the gas sensor of the above-mentioned [1], wherein respective wires in the semiconductor nanowire are bonded with a transparent insulating resin binder,
[3] the gas sensor of the above-mentioned [1] or [2], wherein at least one of the counter electrodes is a transparent electrode,

[4] the gas sensor of the above-mentioned [3], wherein the transparent electrode comprises a transparent insulating layer provided on the inner surface thereof,

[5] the gas sensor of the above-mentioned [3] or [4], wherein one of the counter electrodes is a transparent electrode and a conductive layer is provided on the inner surface of the other electrode,

[6] the gas sensor of any one of the above-mentioned [3]-[5], which has a light source that emits light with energy which is not less than the energy near the bandgap of the semiconductor nanowire, and the light source is arranged on the outside of the transparent electrode,

[7] the gas sensor of the above-mentioned [1] or [2], wherein an insulating layer is formed on the inner surface of one of the counter electrodes, and a conductive layer is formed on the inner surface of the other electrode,

[8] the gas sensor of the above-mentioned [1] or [2], wherein the distal ends of the two conductor wires face each other and the distal ends of the two conductor wires form counter electrodes, and semiconductor nanowires are disposed between the tips of the two conductor wires,

[9] the gas sensor of the above-mentioned [8], wherein the tips of the two conductor wires are led to face each other at a predetermined portion of a transparent insulating member containing a light source that emits light having energy which is not less than the energy near the bandgap of the semiconductor nanowire,

[10] the gas sensor of any one of the above-mentioned [1]-[9], wherein the semiconductor nanowire is a selenium nanowire,

[11] the gas sensor of any one of the above-mentioned [1]-[10], wherein the photoelectric current change is a change in the electric current intensity,

[12] the gas sensor of any one of the above-mentioned [1]-[11], wherein the electric field intensity (absolute value) between the counter electrodes applied with a voltage is 3-34 V/mm,

[13] a gas sensor array comprising a plurality of the gas sensor of any one of the above-mentioned [1]-[12], which are arranged along the gas flow direction of a gas flow path through which a gas to be detected flows,

[14] the gas sensor array of the above-mentioned [13], comprising a single electrode arranged such that its axis is parallel to the gas flow direction of the gas flow path through which the gas to be detected flows, wherein the single electrode is a common electrode used as one of two opposing electrodes of individual gas sensors in the plurality of gas sensors,

[15] the gas sensor array of the above-mentioned [14], wherein the single electrode is a transparent electrode,

[16] the sensor array of any one of the above-mentioned [13]-[15], wherein the gas to be detected that flows in the gas flow path comes into contact, under a constant voltage, with semiconductor nanowires of plural gas sensors to generate time-change spectrum of photoelectric current intensity in each gas sensor, and a delay time between different sensors is detected, and

[17] a gas analysis system comprising the gas sensor array of any one of the above-mentioned [13]-[15], and a calculation part for specifying a gas type, specifying a component ratio of a mixed gas or specifying gas components of a mixed gas, which is based on comparison results of an electric output value based on a change in photoelectric current that occurs in each gas sensor when a gas to be detected is flown in a gas flow path while applying a constant voltage to plural gas sensors in the gas sensor array, and numerical values preserved in a database.

Effect of the Invention

According to the present invention, a semiconductor gas sensor using photoelectric current, particularly, a semiconductor gas sensor using photoelectric current, which can operate at room temperature, can be used repeatedly with low power consumption, and shows sufficiently high sensitivity (sub ppm order) and responsiveness can be provided. In addition, the gas sensor can by provided as a compact gas sensor integrated with luminescence diode.

According to the present invention, moreover, an gas sensor array which operates at room temperature, can be used repeatedly with low power consumption, shows extremely high sensitivity, and has a gaseous species analysis function can be provided.

DESCRIPTION OF EMBODIMENTS

Figure 1:
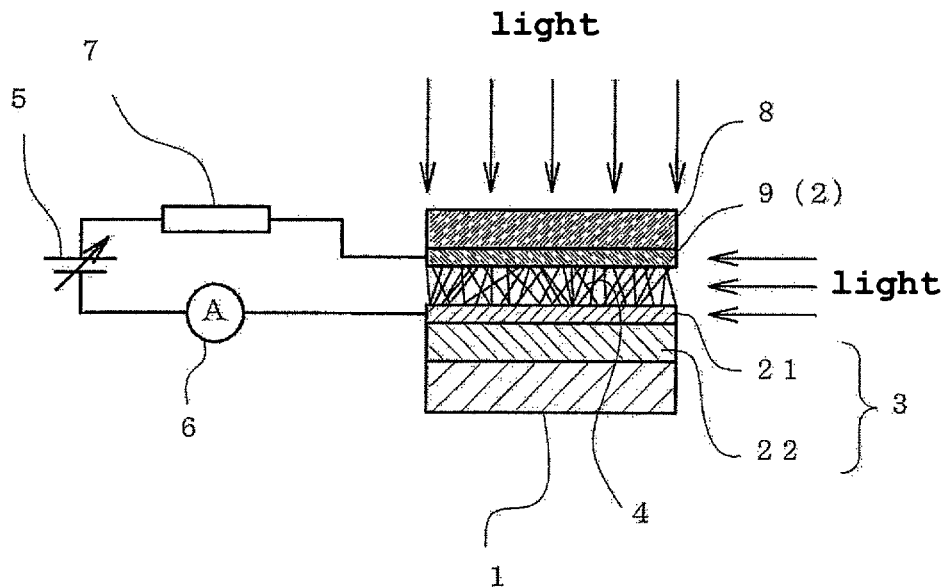
FIG. 1 is a schematic side-view of a first example of the light-transmissive electrode type gas sensor of the present invention.

In the gas sensor of the present invention, a semiconductor nanowire is disposed between counter electrodes (i.e., two opposing electrodes), and measures changes in the electric current associated with adsorption of a gas to the semiconductor nanowire, wherein the electric current is generated by irradiation of light on the semiconductor nanowire with a voltage applied to the counter electrodes.

In the present specification, on the basis of the gap between the counter electrodes of the gas sensor, the side heading toward the gap is referred to as "inside" and the side leaving away from the gap as "outside". Also, the opposing face of the electrode in the counter electrodes is referred to as "the inner face of the electrode" and the face leaving away from the opposing face is referred to as "the outer face of the electrode". Unless otherwise specified, the "counter electrodes" means parallel flat opposing electrodes.

The semiconductor nanowires arranged between the opposing electrodes only need to be in a state where light can be irradiated, and the structure of the sensor therefor is not particularly limited. As a typical example, a configuration in which at least one electrode of the counter electrodes is a transparent electrode, and light passing through the transparent electrode is irradiated on the semiconductor nanowire can be mentioned. This configuration is preferable since light irradiation on the semiconductor nanowires is efficiently and uniformly performed. In addition, when both the counter electrodes are opaque electrodes, a configuration in which light is irradiated from the side of the counter electrodes onto the semiconductor nanowires disposed between the counter electrodes can be mentioned. When at least one electrode of the counter electrodes is a transparent electrode, a configuration in which light passing through the transparent electrode is irradiated onto the semiconductor nanowires, and a configuration in which light is irradiated from the side of the counter electrodes onto the semiconductor nanowires may be used in combination.

When a photoelectric current that flows when light is irradiated on a semiconductor nanowire arranged between counter electrodes is buried in a dark current that flows without irradiating light in the semiconductor nanowire (hereinafter to be also referred to as "base current"), it becomes difficult to measure changes in the photoelectric current associated with adsorption of gas to the semiconductor nanowire. Therefore, in the gas sensor of the present invention, it is important to secure flow of a photoelectric current sufficiently larger than the base current, and a sensor constitution in which the ratio of the measured electric current value by the light irradiation ($I_{ph}+I_b$) and the base current value ($I_b$), (($I_{ph}+I_b$)/$I_b$), is 1.5–70 (preferably 1.8-10) is preferably adopted.

In addition, the electric field intensity E between the counter electrodes influences the sensitivity of the sensor. That is, when the voltage applied to the counter electrodes is high (the electric field intensity E between the counter electrodes is large), while the photoelectric current flows more in the semiconductor nanowire, carriers responsible for the electric current (photoelectric current carriers) cannot be captured efficiently by dipoles that the gas has, since the speed of the carrier is high (that is, photoelectric current carrier near the surface cannot efficiently encounter and be neutralized by electrons (positive holes) injected from the gas). The sensitivity of the sensor is determined by the ratio of photocarriers captured by the electrons (positive holes) injected from the gas. Even if a large amount of photoelectric current flows, the capture efficiency of the photocarrier deteriorates and the sensitivity (S value) of the sensor decreases due to the influence of an increase in the electric field intensity E. Therefore, as is clear from the experimental examples described later, it is important in the gas sensor of the present invention to optimize the electric field intensity E between the counter electrodes from the aspect of sensitivity, and a sensor constitution in which the electric field intensity E between the counter electrodes is 3-34 V/mm (preferably 6-20 V/mm) in absolute value is preferably adopted.

[Semiconductor Nanowire]

In the gas sensor of the present invention, the semiconductor nanowires may be P-type semiconductor nanowires or N-type semiconductor nanowires. Specifically, nanowires such as selenium, tellurium, ZnO, ZnInO, $In_2O_3$, $SiO_2$, $Ga_2O_3$, Ge, Si and the like can be mentioned. Of these, selenium nanowire (hereinafter to be also abbreviated as "SeNW") is preferable since electrons (positive holes) are injected from gas molecules at room temperature without particularly heating and by adsorption of not only inorganic gas but also organic gas. Furthermore, the form of the semiconductor nanowire is not particularly limited. Generally, the "nanowire" refers to a short fiber. However, the "nanowire" in the present invention is a concept including short fiber, long filament (nanofiber), hollow fiber (nanotube), short columnar fiber (nanorod), tabular fiber (nanobelt) and a mixture of two or more kinds of these.

Of these, the semiconductor nanowire is preferably a short fiber nano wire from the aspects of handling, gas adsorption performance, gas desorption performance and the like. While the thickness (diameter) of the semiconductor nanowire is not particularly limited, the average diameter is generally preferably 10 to 600 nm, more preferably 250 to 450 nm. Here, the "average diameter" is the maximum peak value in the diameter distribution of a plurality of samples (number of samples: 50) measured using NI Vision Assistant (software manufactured by National Instruments Corporation) attached to LabVIEW (Laboratory Virtual Instrumentation Engineering Workbench) in the scanning electron microscope (SEM).

In the present invention, one or more kinds of semiconductor nanowires can be used. In the present invention, the most preferable embodiment of the semiconductor nanowire is a short fiber selenium nanowire.

[Counter Electrodes]

For example, gold, silver, copper, aluminum, nickel, ITO (indium tin oxide), tin, chromium, and the like are used for respective electrodes constituting the counter electrodes. While the work function of the semiconductor nanowire is larger than that of the electrode materials, when an electrode material having a work function closer to that of the semiconductor nanowire is used, the ratio of the photoelectric current value to the base current value $I_{ph}/I_b$ tends to be larger. When the semiconductor nanowire is, for example, SeNW, the inner surface of at least one electrode of the counter electrodes is composed of gold in one of the preferable embodiments.

Each electrode constituting the counter electrodes may have a single layer structure or a multi-layer structure. While the thickness of the electrode (total thickness in the case of multi-layer structure) is not particularly limited, it is generally about 100-300 μm. Also, the flat plane area of the electrode is not particularly limited, and it is generally selected from the range of 0.1-0.6 $mm^2$. The flat plane area of the common electrode in an array type gas sensor to be described in detail later (common electrode for a plurality of gas sensors constituting an array) is selected from the range of preferably 0.4-10 $mm^2$.

The amount of semiconductor nanowires present per unit volume on the electrodes between the counter electrodes is preferably not less than 0.4 $mg/mm^3$, more preferably not less than 1.0 $mg/mm^3$, from the aspects of electric conduction between the semiconductor nanowires and the like. It is also preferably not more than 4.8 $mg/mm^3$, more preferably not more than 3.0 $mg/mm^3$, from the aspects of gas contact efficiency with the semiconductor nanowires.

[Light Emitting Means (Light Source)]

To generate a photoelectric current in a semiconductor nanowire, light having energy which is not less than the energy near the bandgap of the semiconductor nanowire (that is, light having energy which is not less than the energy near the bandgap of the semiconductor nanowire) is irradiated on the semiconductor nanowire. Examples of light emitting means for emitting such light include halogen lamp, laser diode (LD), light emitting diode (LED), electroluminescence device (EL), and the like. In the gas sensor, such light emitting means is not necessarily integrated with a sensor part (counter electrode and a semiconductor nanowire arranged therebetween), and a structure in which the light emitted by the light emitting means can reach the semiconductor nanowire between the counter electrodes suffices. Furthermore, the light emitted by such light emitting means may not be used, and a structure in which natural light can reach the semiconductor nanowire between the counter electrodes may be employed.

As used herein, "near the bandgap of the semiconductor nanowire" means that the energy capable of generating a photoelectric current by light absorption of the semiconductor nanowire, that is, a light process including thermal excitation into a conduction band to be a photoconductive current via an impurity level, an exciton level and the like in the semiconductor band gap are also included.

While the irradiation intensity of light on the semiconductor nanowire is not particularly limited, selection of light emitting means, operating conditions of light emitting means, distance between light emitting means and semiconductor nanowires, and the like are preferably adjusted such that the irradiation intensity of light on the semiconductor nanowire is generally not less than 0.05 mW, preferably not less than 0.2 mW, more preferably not less than 1 mW, further preferably not less than 2 mW. While the upper limit of the irradiation intensity of light on the semiconductor nanowire is not particularly limited, not more than 5 mW is preferable, and not more than 2.5 mW is more preferable.

[Measurement Target Gas]

For the gas sensor of the present invention, any gas can be a measurement target as long as it adsorbs to semiconductor nanowires and injects electrons (positive holes) it has into the semiconductor nanowires. Examples of the organic gas include methane, ethane, n-butane, isobutane, 2,2-dimethylbutane, 2,3-dimethylbutane, n-pentane, 2-methylpentane, 2,4-dimethylpentane, n-hexane, 3-methylhexane, n-heptane, 3-methylheptane, nonane, decane, undecane, methylcyclopentane, cyclohexane, methylcyclohexane, ethylcyclohexane, bicyclohexyl, propylene, cis-2-butene, trans-2-butene, 2-methyl-2-butene, 2-methyl-1-butene, 1,3-butadiene, isoprene, cis-2-pentene, trans-2-pentene, 1-heptene, dipentene, benzene, toluene, xylene, 1,3,5-trimethylbenzene, ethylbenzene, cumene, styrene, naphthalene, tetralin, chloromethane, dichloromethane, chloroform, methyl bromide, chloroethane, 1,2-dichloroethane, trichloroethane, trichloroethylene, tetrachloroethylene, tetrafluoroethylene, vinyl chloride, 1,1-dichloroethylene, n-propylbromide, 1,2-dichloropropane, allyl chloride, chlorobenzene, o-dichlorobenzene, methanol, ethanol, isopropanol, n-butanol, isobutanol, ethylene glycol, benzyl alcohol, phenol, methylmercaptan, ethylmercaptan, ethylene glycol monomethylether, ethylcellosolve, isopropylcellosolve, butylcellosolve, propylene glycol monomethylether, propylene oxide, ethylene oxide, epichlorohydrin, tetrahydrofuran, 1,4-dioxane, formic acid methyl, ethyl acetate, trifluoroethyl acetate, propyl acetate, butyl acetate, vinyl acetate, methyl Cellosolve acetate, ethyl Cellosolve acetate, propylene glycol monomethyl ether acetate, propionic acid, acrylic acid, methyl acrylate, methyl methacrylate, acetone, methyl ethyl ketone, methyl isopropyl ketone, methyl isobutyl ketone, methyl n-butyl ketone, methyl amyl ketone, cyclopentanone, cyclohexanone, isophorone, dimethyl sulfoxide, trimethylamine, triethylamine, cyclohexylamine, pyridine, piperidine, formaldehyde, acetaldehyde, acetonitrile, acrylonitrile, N,N-dimethylformamide, N-methyl-2-pyrrolidone, trifluoromethyl propyl ketone and the like. Examples of the inorganic gas include carbon dioxide, carbon monoxide, nitric oxide, nitric dioxide, carbon disulfide, ammonia and the like.

A specific constitution example of the gas sensor is explained below.

1. Light Transmission Electrode Type Gas Sensor

FIG. 1 is a schematic side vies of the first example of the light-transmissive electrode type gas sensor. In the Figure, 1 is a base (nontransparent), 2, 3 are counter electrodes, 4 is a semiconductor nanowire, 5 is a power supply, 6 is an ammeter, 7 is a protective resistor for circuit protection in short circuit, and 8 is a transparent insulating substrate.

Electrode 2 which is one of the counter electrodes is a transparent electrode (e.g., ITO etc.) 9, and the other electrode 3 of the counter electrodes is an opaque electrode with a laminate structure of gold thin film layer 21/copper layer 22.

While the layer thickness of the gold thin film layer 21 is not particularly limited, it is preferably about 3.8-4.0 μm and, while the layer thickness of the transparent electrode 9 is not particularly limited, it is preferably about 25-280 nm.

Electrode 3 can be obtained, for example, by forming a gold thin film on the surface of a copper foil by sputtering, vapor deposition, plating and the like. The close adhesiveness of the gold plating film to the copper foil can be enhanced by performing gold plating after Ni—P alloy plating on the surface of the copper foil.

As transparent insulating substrate 8, for example, glass plate, transparent plastic plate and the like can be used.

While base 1 is not particularly limited as long as it is an insulating material, for example, curable resins such as epoxy resin, polyimide resin, phenol resin and the like, a composite of a curable resin and a glass fiber and the like can be mentioned.

In semiconductor nanowire 4, individual wires may be bonded to each other with a transparent resin binder such as PMMA (polymethyl methacrylate), polyvinyl alcohol (PVA) and the like to prevent scattering of wires and maintenance of an aggregation state of the wires. When bonded, the transparent resin binder not only provides the effects of preventing scattering of the wires and maintaining the aggregation state of the wires, but also shows an action to decrease base current ($I_b$) by functioning as an insulator or a current barrier between wires.

In the gap between the counter electrodes 2 and 3, the amount ratio between the semiconductor nanowire and the transparent resin binder (semiconductor nanowire/transparent resin binder) in a volume ratio is preferably not less than 100/7 and more preferably not less than 100/10 from the aspects of prevention of scattering of the semiconductor nanowires and maintenance of the aggregation state, and the role as an insulator or electric current barrier between wires, and preferably not more than 100/20 and more preferably not more than 100/15 from the aspects of gas contact property with wires.

The gas sensor of the first example has a constitution in which light is irradiated to the semiconductor nanowire through the transparent insulating substrate 8 and the transparent electrode 9, and light is also introduced into the gap between the counter electrodes 2 and 3 on the side portions of the counter electrodes 2 and 3.

In this gas sensor, preferred ranges of the sizes and electric conditions of each part of the sensor that enable measurement of changes in the photoelectric current and optimize electric field intensity between counter electrodes are as follows.

(1) overlap area of counter electrodes (area where opposing surfaces actually overlap): 0.1-0.8 $mm^2$ (preferably 0.1-0.5 $mm^2$)

(2) distance between electrodes of counter electrodes: 0.01-0.30 mm (preferably 0.02-0.07 mm)

(3) voltage applied to counter electrodes: about −100 to +100 V (preferably about −8 to −0.5 V, about +0.5 to +10 V)

In the gas sensor of the first example, since the main carriers contributing to photoconduction are positive holes, the photoelectric current decreases when the semiconductor nanowires come into contact with the electron supply type gas, and the photoelectric current increases on contact with hole supply type gas.

A performance example of the gas sensor of the first example of such light-transmissive electrode type gas sensor is shown below and gas detection in the gas sensor of the present invention is explained.

Figure 2:
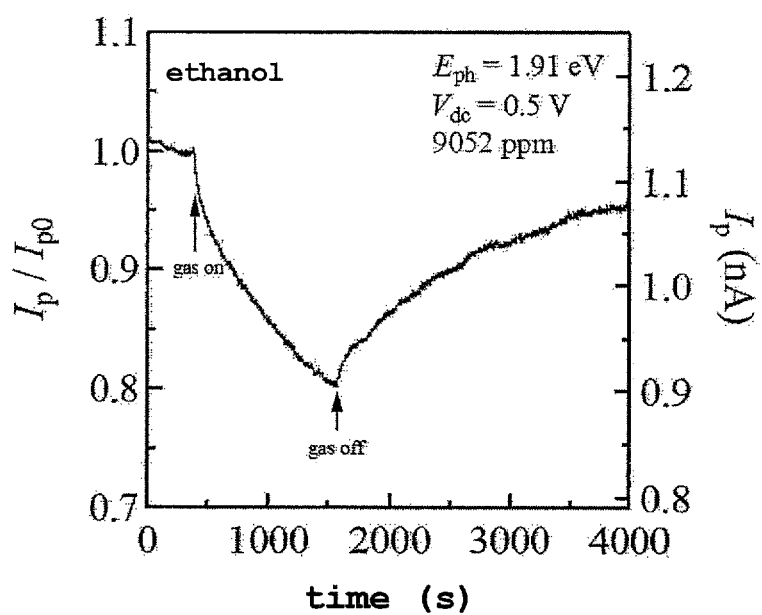
FIG. 2 shows one embodiment of the change in the electric current intensity ratio ($I_P/I_{P0}$) [$I_P=I_{ph}+I_b$, $I_{ph}$ is photoelectric current value, $I_b$ is dark current (base current) value] of photoelectric current value $I_P$ and photoelectric current value $I_{P0}$ before contact with gas, when ethanol gas was contacted with SeNW in the light-transmissive electrode type gas sensor of FIG. 1.

In FIG. 2, a gas sensor wherein the overlap area of the counter electrodes was set to 0.344 $mm^2$, the distance between the electrodes was set to 0.069 mm, SeNW was present between the counter electrodes at 1.56 $mg/mm^3$ was applied with a voltage of 0.5 V, and light from the laser pointer (manufactured by Sakura Crepus Co., Ltd., RX-4, 1 mW type, wavelength: 649 nm, photon energy ($E_{ph}$): 1.91 eV) was irradiated to SeNW at an irradiation intensity of 0.75 mW to photoexcite SeNW to generate a photoelectric current. Changes in the current intensity ratio of the photoelectric current value $I_P$ and the photoelectric current value $I_{P0}$ before contact with gas ($I_P/I_{P0}$) [$I_P=I_{ph}+I_b$] when ethanol gas (mixed gas of ethanol and air with ethanol concentration of 9052 ppm) was brought into contact with SeNW at a flow speed of 0.2 L/min are shown.

Figure 3:
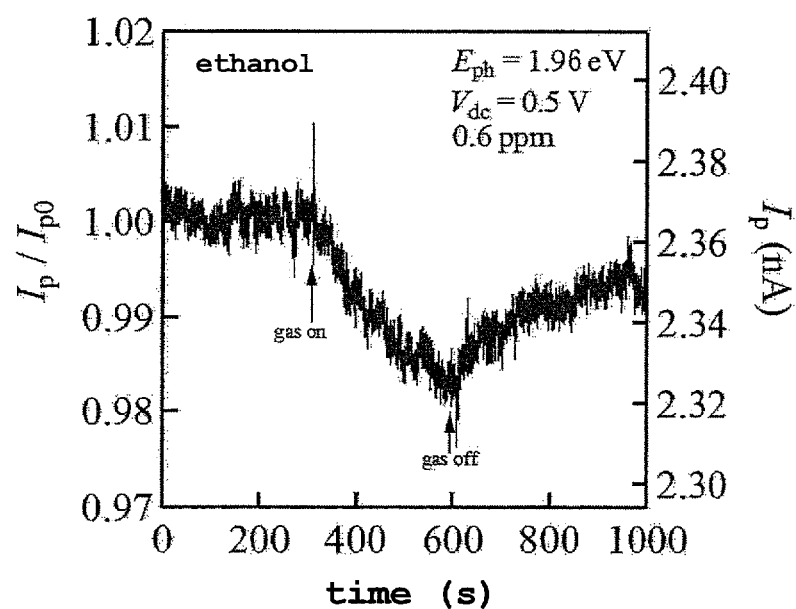
FIG. 3 shows the change in the electric current intensity ratio ($I_P/I_{P0}$) [$I_P=I_{ph}+I_b$] of photoelectric current value $I_P$ and photoelectric current value $I_{P0}$ before contact with gas, when ethanol gas is contacted with SeNW in the light-transmissive electrode type gas sensor of FIG. 1.

In FIG. 3, a voltage of 0.5 V was applied, and light from the He—Ne laser (manufactured by NEC, GLG5370, 3 mW type, wavelength: 633 nm, photon energy ($E_{ph}$):1.96 eV) was irradiated to SeNW at an irradiation intensity of 2.14 mW to photoexcite SeNW to generate a photoelectric current. Changes in the current intensity ratio of the photoelectric current value Ip and the photoelectric current value $I_{P0}$ before contact with gas ($I_P/I_{P0}$) when ethanol gas (mixed gas of ethanol and air with ethanol concentration of 0.6 ppm) was brought into contact with SeNW at a flow speed of 0.2 L/min are shown.

From FIGS. 2, 3, it is found that when SeNW is brought into contact with ethanol gas which is an electron supply type gas (gas on in Figure), the photoelectric current value (electric current intensity ratio of photoelectric current value $I_P$ and photoelectric current value $I_{P0}$ before contact with gas ($I_P/I_{P0}$)) decreases, and the photoelectric current value (electric current intensity ratio of photoelectric current value $I_P$ and photoelectric current value $I_{P0}$ before contact with gas ($I_P/I_{P0}$)) returns to the original value when the ethanol gas contact disappears (gas off in Figure). In particular, FIG. 3 shows that changes in photoelectric current value (electric current intensity ratio of photoelectric current value $I_P$ and photoelectric current value $I_{P0}$ before contact with gas ($I_P/I_{P0}$)) associated with adsorption of gas to SeNW clearly appear even when the concentration of gas is low.

As described above, in the gas sensor of the present invention, when the gas contacts the semiconductor nanowire, the photoelectric current value (electric current intensity ratio of photoelectric current value $I_P$ and photoelectric current value $I_{P0}$ before contact with gas ($I_P/I_{P0}$)) changes along with the adsorption of the gas to the semiconductor nanowire. Therefore, by measuring the change in the photoelectric current value (electric current intensity ratio of photoelectric current value $I_P$ and photoelectric current value $I_{P0}$ before contact with gas ($I_P/I_{P0}$)), Gas can be detected.

FIGS. 2 and 3 show changes in the photoelectric current value associated with the contact and the absence of contact of SeNW with ethanol gas, which is an electron supply type gas. In the case of a positive hole supply type gas (e.g., nitrogen dioxide etc.), changes in the electric current intensity ratio of photoelectric current value $I_P$ and photoelectric current value $I_{P0}$ before contact with gas ($I_P/I_{P0}$) show a behavior inverse to that in FIGS. 2 and 3, since the photoelectric current value increases.

Figure 4:
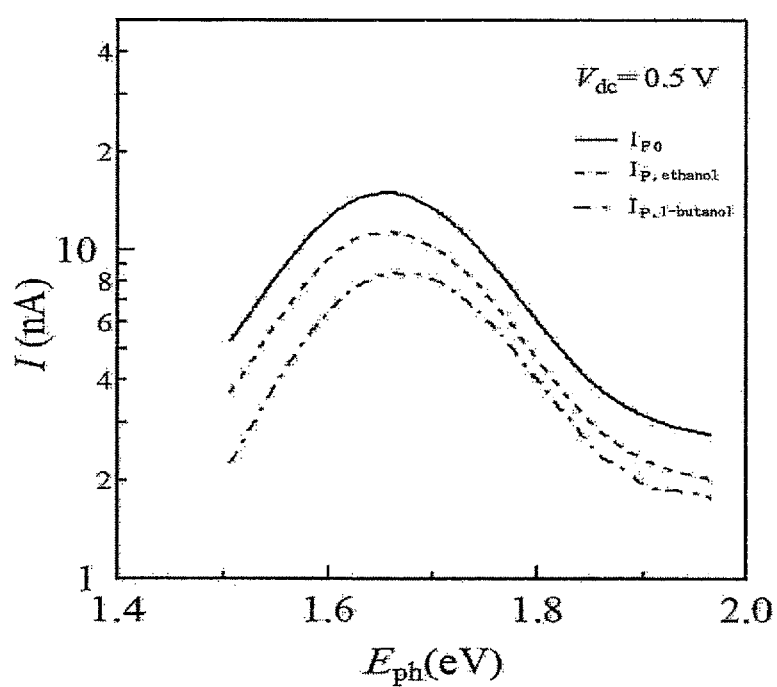
FIG. 4 shows example performance of the light-transmissive electrode type gas sensor of FIG. 1, and shows photoelectric current spectrum (solid line, $I_{P0}$) when ethanol gas was not contacted with SeNW, photoelectric current spectrum (broken line, $I_{P,ethanol}$) when ethanol gas was contacted with SeNW and photoelectric current spectrum (dashed line, $I_{P,1}$-butanol) when 1-butanol gas was contacted with SeNW.

In FIG. 4, the gas sensor of the first example was used, wherein light from a halogen lamp (12 V, 150 W, peak wavelength: 689 nm) was irradiated to SeNW at an average irradiation intensity of 70 µW/mm² to photoexcite SeNW to generate photoelectric current, and a photoelectric current spectrum (solid line, $I_{P0}$) when ethanol gas was not contacted with SeNW, photoelectric current spectrum (broken line, $I_{P,ethanol}$) when ethanol gas was contacted with SeNW and photoelectric current spectrum (dashed line, $I_{P,1-butanol}$) when 1-butanol gas was contacted with SeNW is shown.

From FIG. 4, it is understood that the photoelectric current value (electric current intensity of photoelectric current ($I_{P,1-butanol}$)) when 1-butanol gas contacts SeNW is smaller than the photoelectric current value (electric current intensity of photoelectric current ($I_{P,ethanol}$)) when ethanol gas contacts SeNW. Therefore, in the gas sensor of the present invention, it is obvious that the behavior of the change in the electric current intensity ($I_{P,1-butanol}$) of the photoelectric current caused by the contact and the absence of contact of semiconductor nanowire with the gas varies depending on the type of gas.

Figure 5:
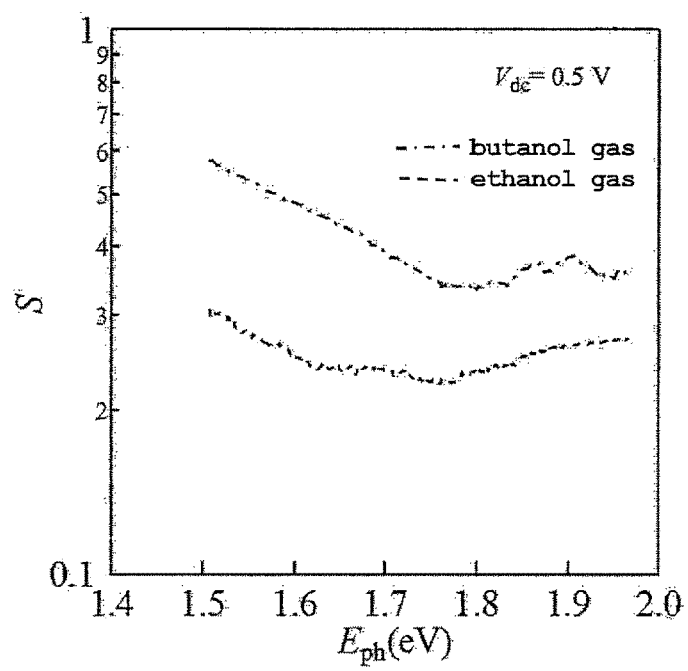
FIG. 5 shows energy (photon energy ($E_{ph}$)) dependency of sensor sensitivity S in the light-transmissive electrode type gas sensor of FIG. 1, as calculated using the results of FIG. 4.

FIG. 5 shows the energy (photon energy) dependency of the sensor sensitivity S as calculated using the experimental results of FIG. 4. The sensor sensitivity S here is $S=\Delta I_P/I_{P0}$, wherein the change in the electric current value $\Delta I_P=(I_{P0}-I_{Pi})$ [$I_{Pi}$ is photoelectric current value of ethanol gas or 1-butanol gas due to the contact with gas] is normalized with the photoelectric current spectrum $I_{P0}$ in a state free of contact with gas (blank).

This Figure shows that, even when light of energy in the vicinity of the bandgap near (around 1.6 eV) of SeNW is irradiated to SeNW, it functions as a sensor, and moreover, the sensor sensitivity S becomes about three times higher than irradiation of light with energy not less than the band gap. This is considered to be because the light of energy in the vicinity of the bandgap can enter into the inside of the crystal of the semiconductor nanowire.

As described above, in the gas sensor of the present invention, it is also possible to identify the type of gas from the difference in the level of change, that is, sensor sensitivity S, by measuring the changes in the current value $\Delta I_P$ of the photoelectric current.

Figure 6:
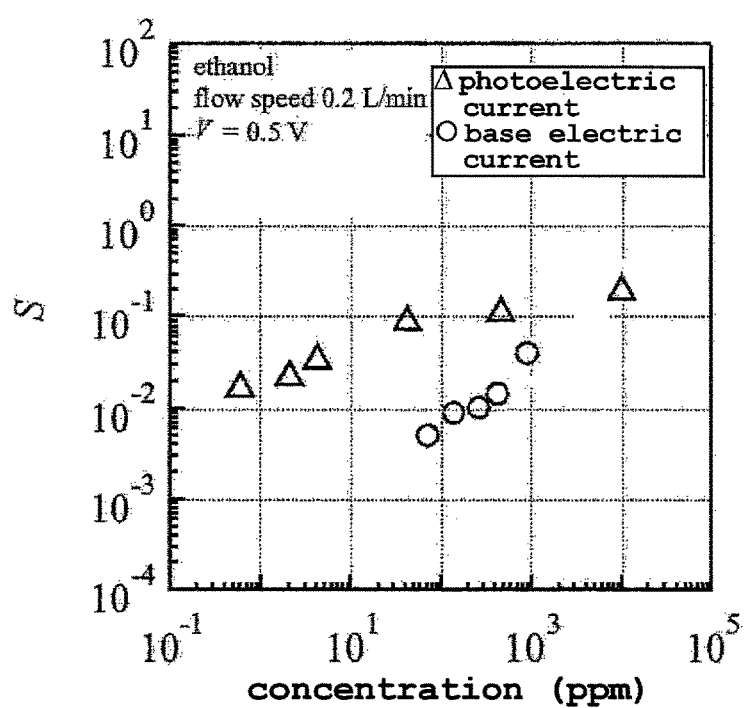
FIG. 6 shows the relationship between ethanol gas concentration and sensor sensitivity S in the light-transmissive electrode type gas sensor of FIG. 1. In the Figure, the plot Δ shows sensitivity S based on the photoelectric current that flows in SeNW, and the plot ○ shows sensitivity S based on the base current that flows in SeNW of conventional gas sensor free of light irradiation.

In FIG. 6, application voltage (0.5 V) was applied between the counter electrodes, and light from the aforementioned laser pointer (manufactured by Sakura Crepus Co., Ltd., RX-4, 1 mW type, wavelength: 649 nm, photon energy ($E_{ph}$) 1.91 eV) was irradiated to SeNW at the maximum and constant irradiation intensity to photoexcite SeNW. The relationship between ethanol gas concentration and sensitivity S when ethanol gas (mixed gas of ethanol gas and air having an ethanol gas concentration of 0.6 ppm-9052 ppm) was flown in SeNW at a flow speed of 0.2 L/min is shown. In the Figure, the sensitivity S (plot ○) of the gas sensor (gas sensor that measures changes in the electric current associated with gas adsorption to SeNW of the base current flowing through the SeNW, without irradiating SeNW with light) corresponding to the conventional gas sensor described in patent document 1, as well as sensitivity S (plot Δ) of this Example is also shown.

It can be seen from FIG. 6 that the gas sensor exhibits an intrinsic sensitivity S relative to the concentration of gas to be in contact with SeNW. Therefore, the gas sensor of the present invention can detect concentration of a specific gas in the gas air. It is also possible to obtain sensitivity at 1 ppm or below, which was not measureable heretofore. The sensor sensitivity S here is $S=\Delta I_P/I_{P0}$, wherein the change in the electric current value $\Delta I_P=(I_{P0}-I_{Pm})$ [$I_{Pm}$ is minimum value of ethanol gas or 1-butanol gas due to the contact with gas] is normalized with the photoelectric current spectrum $I_{P0}$ in a state free of contact with gas (blank).

Figure 7:
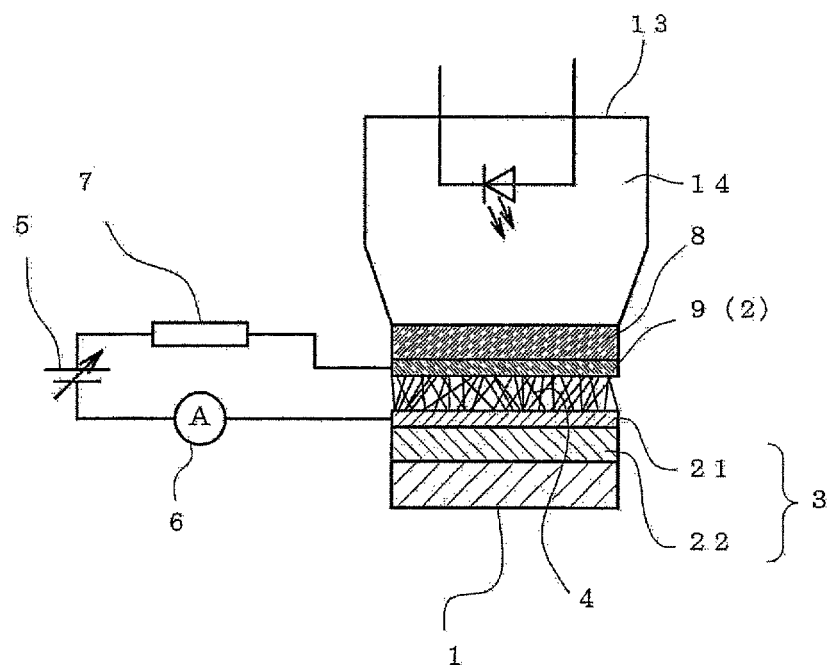
FIG. 7 is a schematic side view of a second example of the light-transmissive electrode type gas sensor of the present invention.

FIG. 7 shows a schematic side view of a second example of a light-transmissive electrode type gas sensor. In the Figure, the same reference numerals as those in FIG. 1 denote the same or corresponding parts, and 13 is an LED chip with a tip of a dome type sealing resin (transparent resin) cut to form a flat surface. The transparent insulating substrate 8 and the sealing resin (transparent resin) 14 of the LED chip 13 may be adhesion-fixed with a transparent adhesive (not shown).

In this sensor, since the light source (LED) is disposed in the vicinity of the semiconductor nanowire 4, attenuation of the intensity of the excitation light up to the arrival at the semiconductor nanowire 4 is small and the semiconductor nanowire 4 can be excited efficiently.

Figure 8:
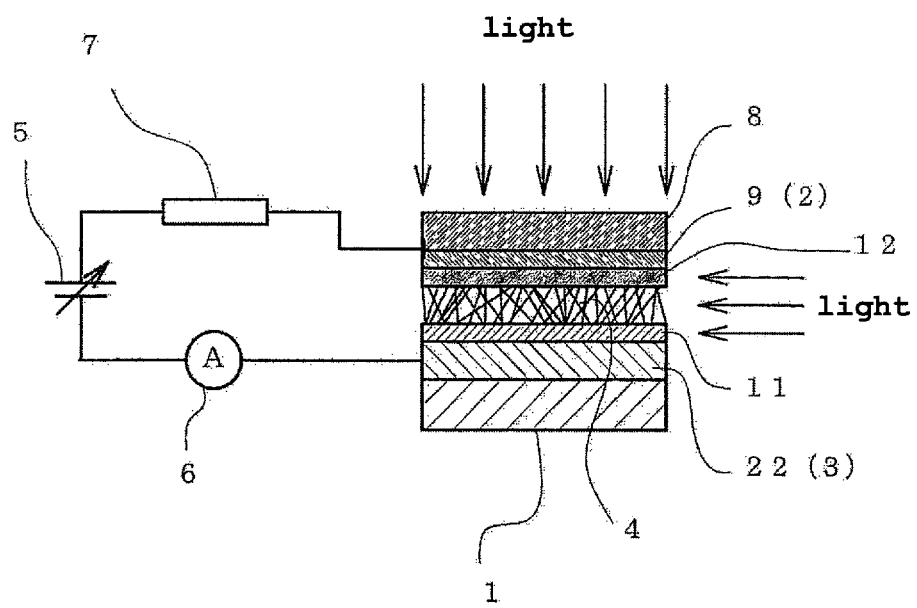
FIG. 8 is a schematic side view of a third example of the light-transmissive electrode type gas sensor of the present invention.

FIG. 8 is a schematic side view of a third example of the light-transmissive electrode type gas sensor.

In the Figure, the same symbols as in FIG. 1 show the same or corresponding parts. 12 is a transparent insulating layer, and 11 is a conductive layer.

As the transparent insulating layer 12, for example, PMMA layer, mica layer and the like are used. The thickness of the transparent insulating layer 12 is generally 0.1-3.0 µm (preferably 0.4-2.0 µm). The conductive layer 11 preferably has an impedance per square inch of about 0-50Ω, and preferably has adhesiveness (that is, adhesive conductive layer). The thickness is preferably about 0.05-0.25 mm. Specific examples of the adhesive conductive layer include a carbon tape (double-sided pressure-sensitive adhesive tape containing carbon powder as conductive filler). Since the conductive layer 11 is an adhesive conductive layer, not only conductiveness but also prevention of the scattering of the semiconductor nanowires and maintenance of an aggregation state of the wires can be achieved.

In this gas sensor, the current flowing between the electrode 2 (transparent electrode 9) and the electrode 3 (copper electrode 22) is hindered by the transparent insulating layer 12. Therefore, the optimum amount of electric current of the photoelectric current and the base current ($I_b$) can be secured by forming a conductive layer 11 which promotes a dramatic improvement in the conduction efficiency relative to the semiconductor nanowire. When the transparent insulating layer 12 is absent and only the conductive layer 11 is used, such optimization cannot be achieved and the photoelectric current ($I_{ph}$) is buried in the base current ($I_b$). When both the transparent insulating layer 12 and the conductive layer 11 are used, only the electric field by the electrode 2 and the electrode 3 can be effectively applied to the optical carrier generated by light irradiation on the semiconductor nanowire. Thus, the photoelectric current generated in the semiconductor nanowire by light irradiation can be efficiently captured into the electrode 3 side by the conductive layer 11.

When the electrode 2 (transparent electrode 9) is positive relative to the electrode 3 (copper electrode 22), fluctuation of the measured electric current can be reduced by making the electric current to the ammeter an electric current in only one direction by placing a diode between the ammeter 6 and the electrode 3 (copper electrode 22).

In the gas sensor of the first example free of the conductive layer 11 (FIG. 1), it substantially has a small diode since a Schottky barrier is formed between the semiconductor nanowire 4 and the metal of the electrode 3. However, in the gas sensor of this example having the conductive layer 11 (FIG. 8), the electric current passes well since the Schottky barrier disappears. On the other hand, the electric current noise due to the influence of the reverse current generated by light tends to increase. For this reason, it is preferable to provide a diode on the outside of the counter electrodes.

In this gas sensor (FIG. 8), preferred ranges of the sizes and electric conditions of each part of the sensor that enable measurement of changes in the photoelectric current and optimize electric field intensity between counter electrodes are as follows.
(1) overlap area of counter electrodes (area where opposing surfaces actually overlap): 0.1-0.8 mm$^2$ (preferably 0.1-0.5 mm$^2$)
(2) distance between electrodes of counter electrodes: 0.01-0.5 mm (preferably 0.08-0.3 mm)
(3) voltage applied to counter electrodes: about −10 to +10 V (preferably about −8 to −0.5 V, about +0.5 to +10 V)

Figure 9:
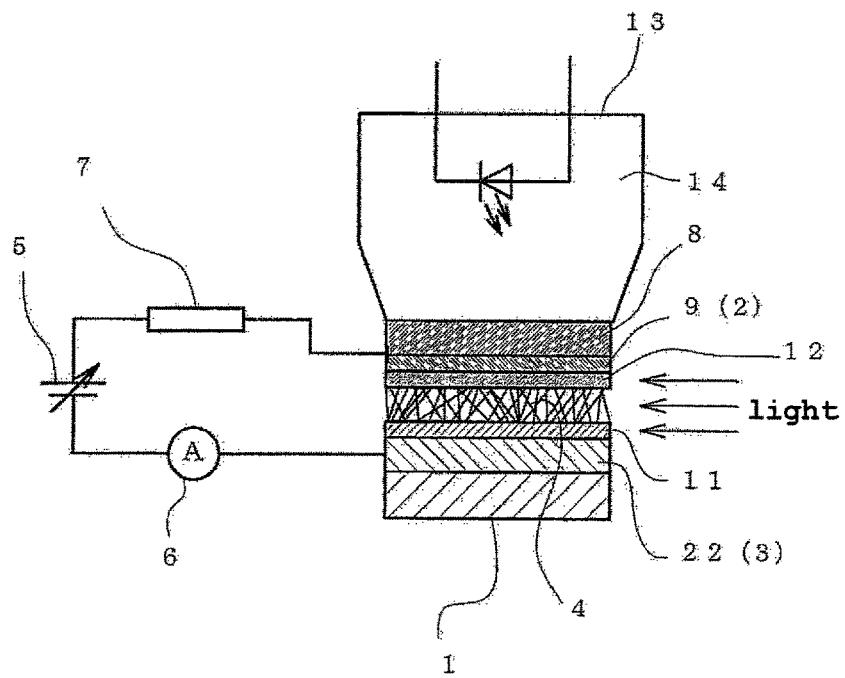
FIG. 9 is a schematic side view of a fourth example of the light-transmissive electrode type gas sensor of the present invention.

FIG. 9 is a schematic side view of the fourth example of the light-transmissive electrode type gas sensor. In the Figure, the symbols same as those in FIGS. 7 and 8 mean the same or the corresponding parts. Similar to the gas sensor of the second example (FIG. 7), since the light source (LED) is disposed in the vicinity of the semiconductor nanowire 4 in this sensor, attenuation of the intensity of the excitation light up to the arrival at the semiconductor nanowire 4 is small and the semiconductor nanowire 4 can be excited efficiently.

In this gas sensor (FIG. 9), preferred ranges of the sizes and electric conditions of each part of the sensor that enable measurement of changes in the photoelectric current and optimize electric field intensity between counter electrodes are as follows.
(1) overlap area of counter electrodes (area where opposing surfaces actually overlap): 0.1-0.8 mm$^2$ (preferably 0.1-0.5 mm)
(2) distance between electrodes of counter electrodes: 0.01-0.5 mm (preferably 0.08-0.3 mm)
(3) voltage applied to counter electrodes: about −10 to +10 V (preferably about −8 to −0.5 V, about +0.5 to +10 V)

Figure 10:
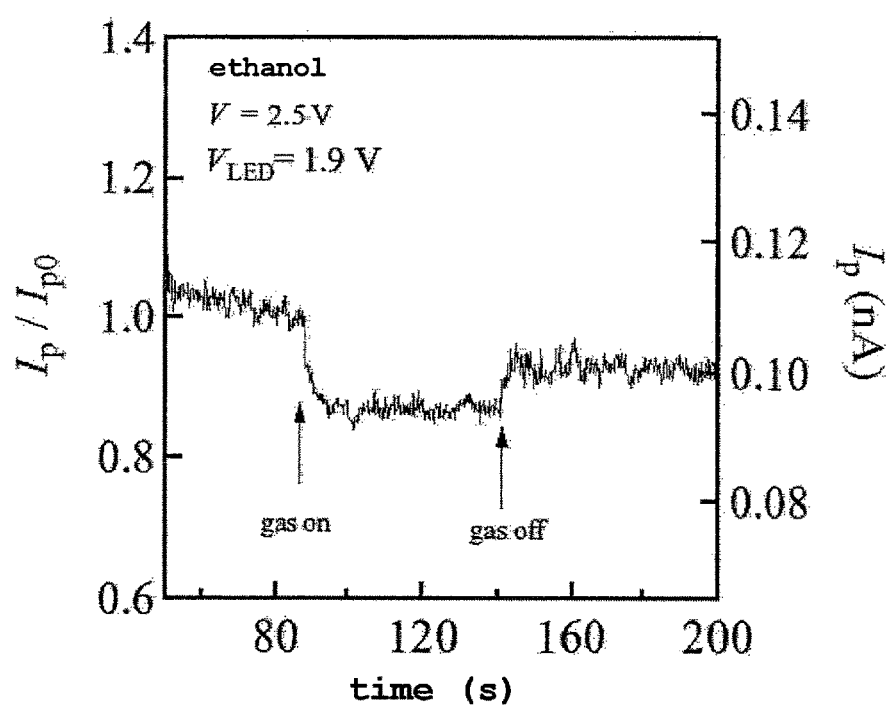
FIG. 10 shows one embodiment of the change in the electric current intensity ratio ($I_P/I_{P0}$) [$I_P=I_{ph}+I_b$] of photoelectric current value $I_P$ and photoelectric current value $I_{P0}$ before contact with gas, when ethanol gas is contacted with SeNW in the light-transmissive electrode type gas sensor of FIG. 9.

A performance example of this gas sensor is shown. Overlap area of counter electrodes: 0.5×0.5 mm$^2$, thickness of transparent insulating layer: 1.66 µm, semiconductor nanowire: SeNW (2 mg/mm$^3$), distance between the electrodes of counter electrodes: 0.146 mm, application voltage: 2.5 V, and light excitation intensity by LED (Avago HLMP-C115, 637 nm): 3.1 mW were set, and SeNW was photo-excited to generate photoelectric current, and ethanol gas was brought into contact with SeNW. The ethanol gas was supplied by setting the tip of a cotton swab impregnated with ethanol at a position 1 mm away from the gas sensor. FIG. 10 shows changes in the electric current intensity ratio between the photoelectric current value $I_P$ at this time and the photoelectric current value $I_{P0}$ before contact with the gas ($I_P/I_{P0}$) [$I_P=I_{ph}+I_b$].

Figure 16:
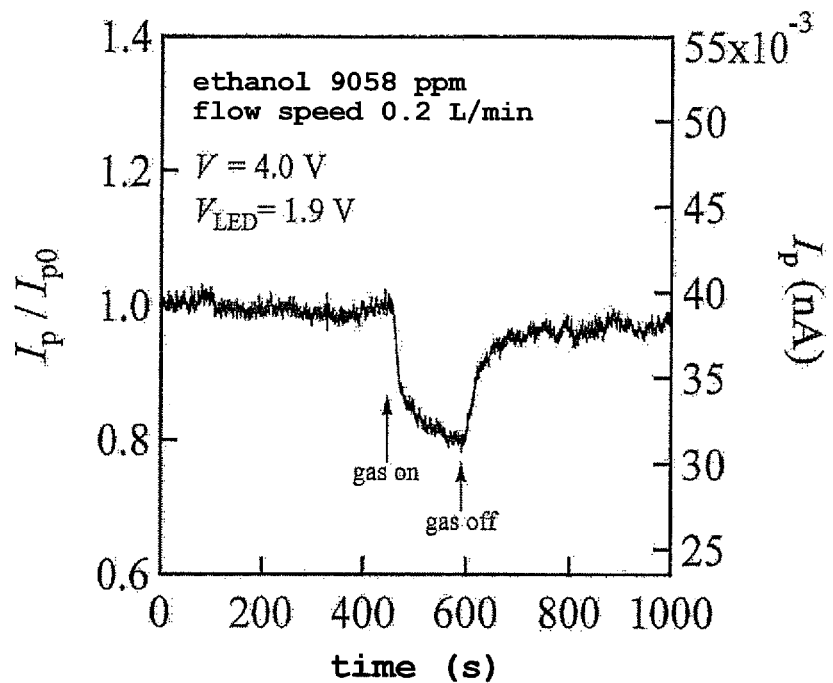
FIG. 16 shows the change in the electric current intensity ratio ($I_P/I_{P0}$) [$I_P=I_{ph}+I_b$] of photoelectric current value $I_P$ and photoelectric current value $I_{P0}$ before contact with gas, when ethanol gas (mixed gas of ethanol with ethanol concentration of 9058 ppm and air) was contacted with SeNW in the wire electrode type gas sensor of FIG. 15.

It is clear that the gas response speed is fast as compared to the change in the electric current intensity ratio of photoelectric current value $I_P$ and photoelectric current value before contact with the gas $I_{P0}$ ($I_P/I_{P0}$) in the wire electrode type gas sensor described below (FIG. 16). This suggests that an efficient electric field is applied when both the transparent insulating layer and the conductive layer are used, as well as the generated photocarriers can be taken out efficiently from the conductive layer.

Figure 11:
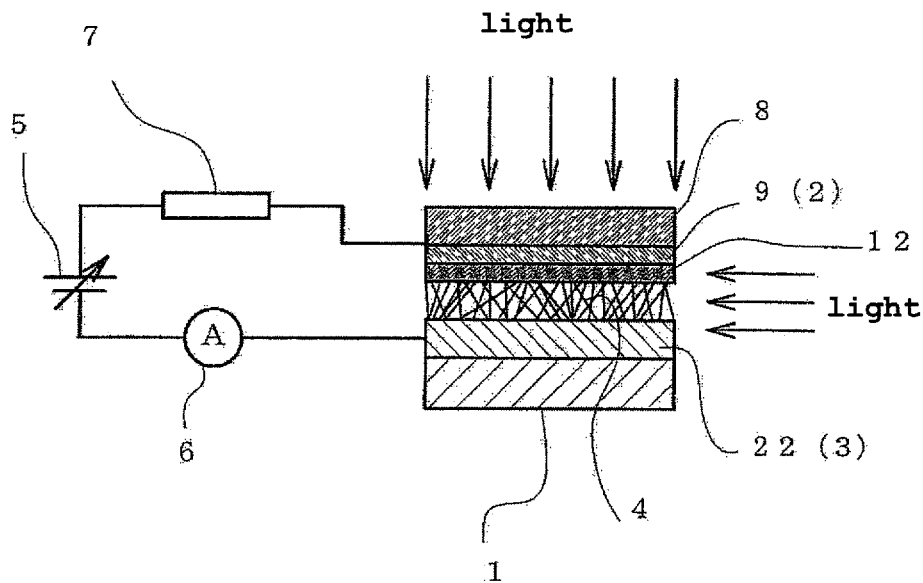
FIG. 11 is a schematic side view of a fifth example of the light-transmissive electrode type gas sensor of the present invention.

FIG. 11 is a schematic side view of the fifth example of the light-transmissive electrode type gas sensor. In the Figure, the symbols same as those in FIG. 7 mean the same or the corresponding parts. This gas sensor has a constitution of the gas sensor of the second example (FIG. 7) added with a transparent insulating layer 12.

In this gas sensor, preferred ranges of the sizes and electric conditions of each part of the sensor that enable measurement of changes in the photoelectric current and optimize electric field intensity between counter electrodes are as follows.
(1) overlap area of counter electrodes (area where opposing surfaces actually overlap): 0.1-0.8 mm$^2$ (preferably 0.1-0.5 mm$^2$)
(2) distance between electrodes of counter electrodes: 0.01-0.5 mm (preferably 0.08-0.3 mm)
(3) voltage applied to counter electrodes: about −10 to +10 V (preferably about −8 to −0.5 V, about +0.5 to +10 V)

Figure 12:
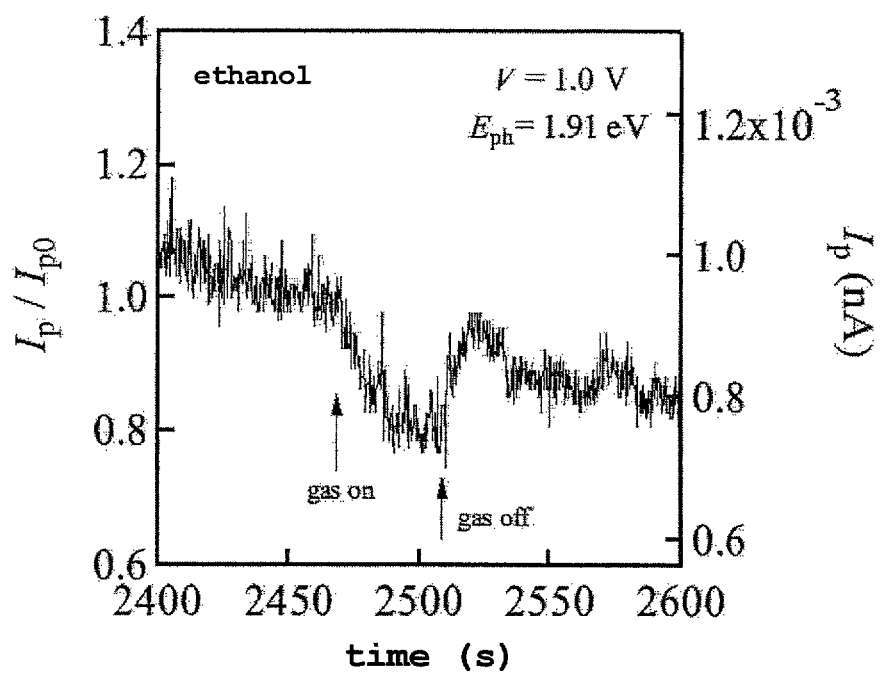
FIG. 12 shows one embodiment of the change in the electric current intensity ratio ($I_P/I_{P0}$) [$I_P=I_{ph}+I_b$] of photoelectric current value $I_P$ and photoelectric current value $I_{P0}$ before contact with gas, when ethanol gas is contacted with SeNW in the light-transmissive electrode type gas sensor of FIG. 11.

A performance example of this gas sensor is shown. Overlap area of counter electrodes: 0.5×0.5 mm$^2$, thickness of transparent insulating layer: 0.30 µm, semiconductor nanowire: SeNW (2 mg/mm$^3$), distance between the electrodes of counter electrodes: 0.091 mm, application voltage: 1.0 V, light source: laser pointer (manufactured by Sakura Crepes Co., Ltd., RX-4, 1 mW type, wavelength: 649 nm, photon energy ($E_{ph}$): 1.91 eV) were set, and SeNW was irradiated at an irradiation intensity of 0.75 mW to photoexcite SeNW to generate photoelectric current, and ethanol gas was brought into contact with SeNW. The ethanol gas was supplied by setting the tip of a cotton swab impregnated with ethanol at a position 1 mm away from the gas sensor. FIG. 12 shows changes in the current intensity ratio between the photoelectric current value $I_P$ at this time and the photoelectric current value $I_{P0}$ before contact with the gas ($I_P/I_{P0}$) [$I_P=I_{ph}+I_b$].

In the present invention, the light-transmissive electrode type gas sensor can have a constitution of the gas sensor of the first example (FIG. 1) added with only a conductive layer 11 (constitution of FIG. 8 but excluding the transparent insulating layer 12). Also, it can be a constitution of the first example (FIG. 1) added with only the transparent insulating layer 12 (constitution of FIG. 8 but excluding the conductive layer 11).

2. Light Impermeable Electrode Type Gas Sensor

In the light impermeable electrode type gas sensor, light is irradiated on the semiconductor nanowire from the gap between the side portions of the counter electrodes.

Figure 13:
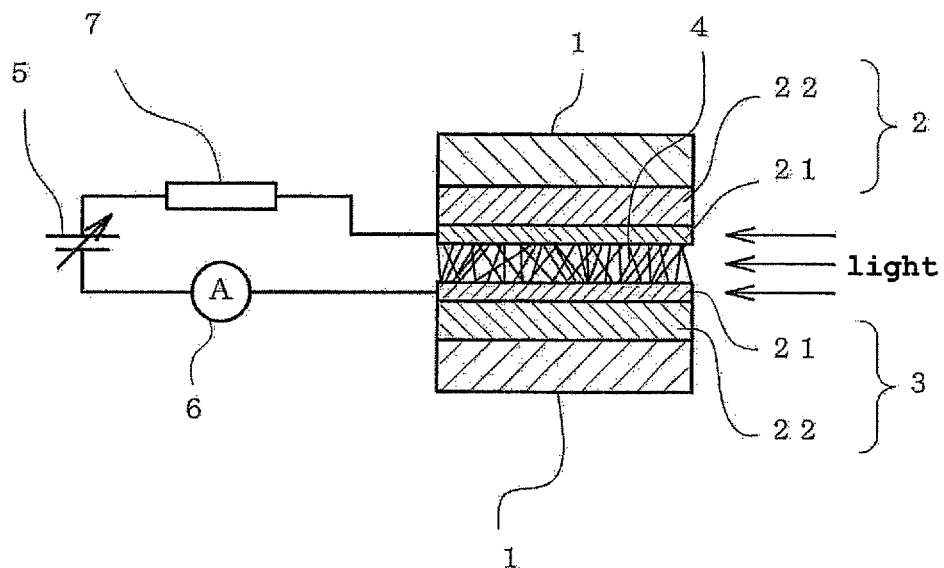
FIG. 13 is a schematic side view of a first example of the light impermeable electrode type gas sensor of the present invention.

FIG. 13 is a schematic side view of the first example of the light impermeable electrode type gas sensor. In the Figure, the symbols same as those in FIG. 1 mean the same or the corresponding parts. Each of the counter electrodes 2, 3 is constituted of a non-transparent electrode having a laminate constitution of gold thin film layer 21/copper layer 22.

In this gas sensor, preferred ranges of the sizes and electric conditions of each part of the sensor that enable measurement of changes in the photoelectric current and optimize electric field intensity between counter electrodes are as follows.

(1) overlap area of counter electrodes (area where opposing surfaces actually overlap): 0.1-0.8 mm$^2$ (preferably 0.1-0.5 mm$^2$)

(2) distance between electrodes of counter electrodes: 0.01-0.50 mm (preferably 0.02-0.07 mm)

(3) voltage applied to counter electrodes: about −100 to +100 V (preferably about −8 to 0.5 V, about +0.5 to +10 V)

Figure 14:
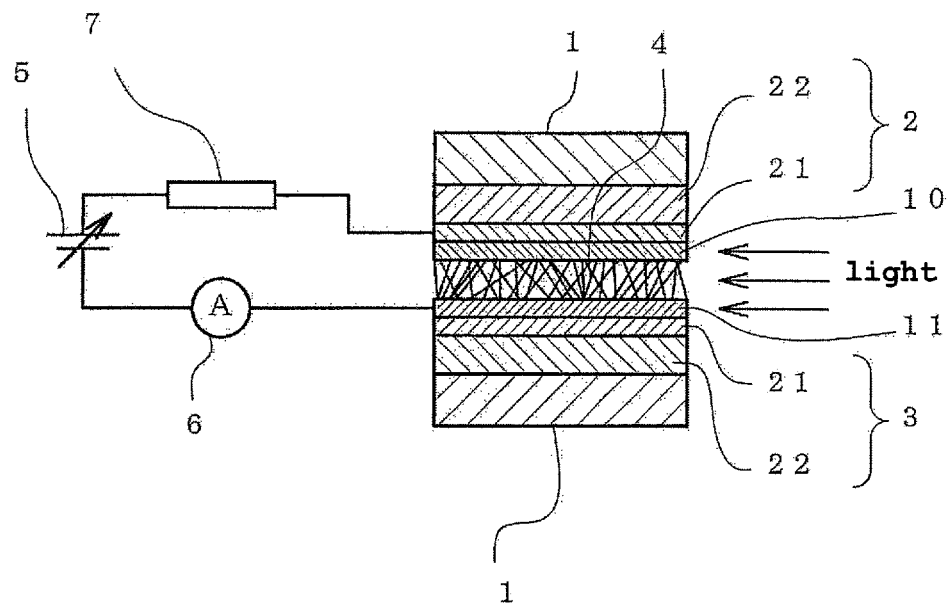
FIG. 14 is a schematic side view of a second example of the light impermeable electrode type gas sensor of the present invention.

FIG. 14 is a schematic side view of the second example of the light impermeable electrode type gas sensor. In the Figure, the symbols same as those in FIG. 13 mean the same or the corresponding parts. An insulating layer 10 is formed on the inner surface of one electrode 2 of the counter electrodes, a conductive layer 11 is formed on the inner surface of the other electrode 3, and a semiconductor nanowire 4 is interposed between the insulating layer 10 and the conductive layer 11.

As the insulating layer 10, a polymer layer made of acrylic resin such as PMMA and the like, fluororesin such as polyester, polypropylene, polycarbonate, polystyrene, Teflon, and the like, and a ceramic layer made of mica, alumina ($Al_2O_3$), tantalum oxide, titanium oxide, barium titanate, strontium titanate and the like can be mentioned. Of these, PMMA and mica are preferable since they are transparent to the visible light. The thickness of the insulating layer 10 is preferably about 0.1-3.0 μm. Particularly, in the case of PMMA layer, the layer thickness is preferably not less than 150 nm, more preferably not less than 260 nm, from the aspects of the insulation performance, and, to facilitate passage of the leakage electric current to some extent, it is preferably not more than 1000 nm, more preferably not more than 500 nm.

As the conductive layer 11, those similar to the conductive layer 11 in the gas sensor of the third example of the light-transmissive electrode type gas sensor (FIG. 8) are used.

In the gas sensor of the second example, the conduction efficiency of the semiconductor nanowire 4 is dramatically improved by the conductive layer 11, and the base current ($I_b$) is increased. Since the photoelectric current ($I_{ph}$) is buried in the base current ($I_b$) as it is, the insulating layer 10 is formed on the electrode opposite to the electrode provided with the conductive layer 11.

In this gas sensor, preferred ranges of the sizes and electric conditions of each part of the sensor that enable measurement of changes in the photoelectric current and optimize electric field intensity between counter electrodes are as follows.

(1) overlap area of counter electrodes (area where opposing surfaces actually overlap): 0.1-0.8 mm$^2$ (preferably 0.15-0.35 mm$^2$)

(2) distance between electrodes of counter electrodes: 0.05-0.30 mm (preferably 0.12-0.26 mm)

(3) voltage applied to counter electrodes: about −100 to +100 V (preferably about −10 to +10 V)

3. Wire Electrode Type Gas Sensor

Figure 15:
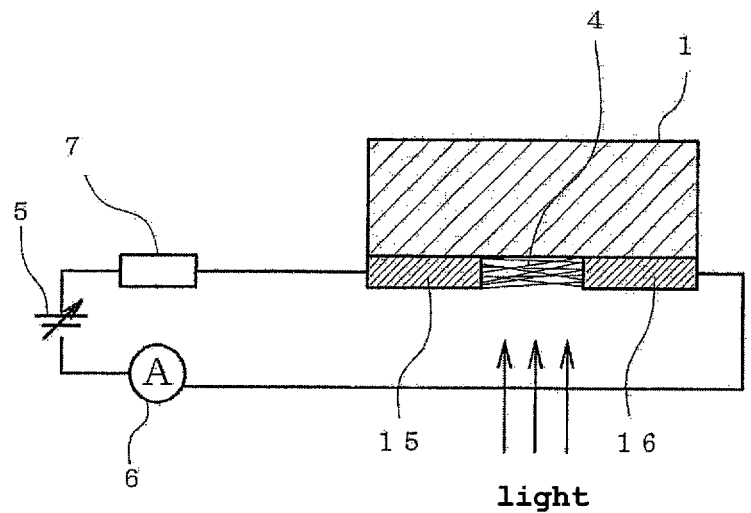
FIG. 15 shows a schematic side view (FIG. 15(a)) and a schematic flat plane FIG. 15(b)) of the wire electrode type gas sensor of the present invention.
Figure 15:
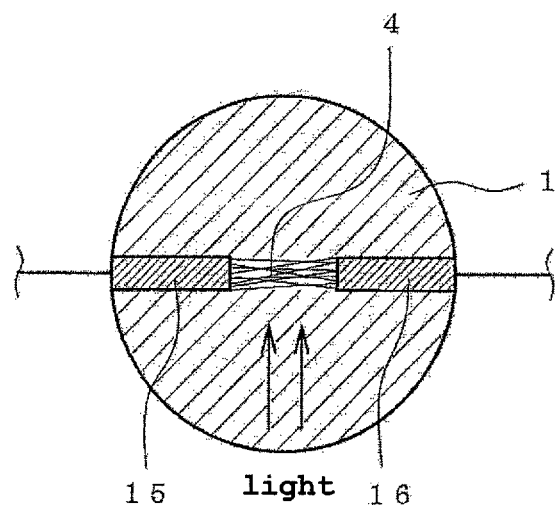

FIG. 15 shows a schematic side view (FIG. 15(a)) and a schematic flat plane view (FIG. 15(b)) of the wire electrode type gas sensor. In the Figure, the symbols same as those in FIG. 1 mean the same or the corresponding parts. Two conductor wires 15 and 16 (e.g., copper wire, gold wire, tin-plated copper wire, copper wire, etc.) are guided on the base 1 such that their tips face each other, the tips of the two conductor wires 15 and 16 form the counter electrodes, and the semiconductor nanowire 4 is arranged between the tips of the two conductor wires 15 and 16.

In the wire electrode type gas sensor of FIG. 15, a combination of an insulating layer and a conductive layer may be provided as in FIG. 14. Alternatively, an insulating layer may be provided only on the tip (electrode) of one wire.

In this gas sensor, preferred ranges of the sizes and electric conditions of each part of the sensor that enable measurement of changes in the photoelectric current and optimize electric field intensity between counter electrodes are as follows.

(1) distance between the opposing tips of two conductor wires: about 0.1-0.5 mm (preferably about 0.2-0.4 mm)

(2) voltage applied to two conductor wires: about −10 to +10 V (preferably about −2 to −5 V, about +2 to 5 V)

A performance example of this wire electrode type gas sensor is shown below.

Using a roll wire for wire wrapping (cord outer diameter 0.9 mm, cord copper wire diameter (diameter) 0.6 mm, manufactured by Ebrene Co., Ltd.) as two conductor wires 15 and 16, and setting the distance between the opposing tips of two conductor wires 15 and 16 to 0.35 mm, 20 μg of SeNW was placed between the opposing tips, an applied voltage of 4.0 V is applied to the two conductor wires 15 and 16, LED (Avago HLMP-C115, 637 nm) chip was operated with voltage ($V_{LED}$) 1.9 V with a dry cell, SeNW was irradiated with light from the LED chip at an irradiation intensity of 3.1 mW to photoexcite SeNW to generate photoelectric current, and ethanol gas (mixed gas of ethanol and air with an ethanol concentration of 9058 ppm, flow speed 0.2 L/min) was brought into contact with SeNW. FIG. 16 shows changes in the electric current intensity ($I_P/I_{P0}$) of the photoelectric current then. It is clear that the response rate is slow even though the gas had high concentration.

Figure 17:
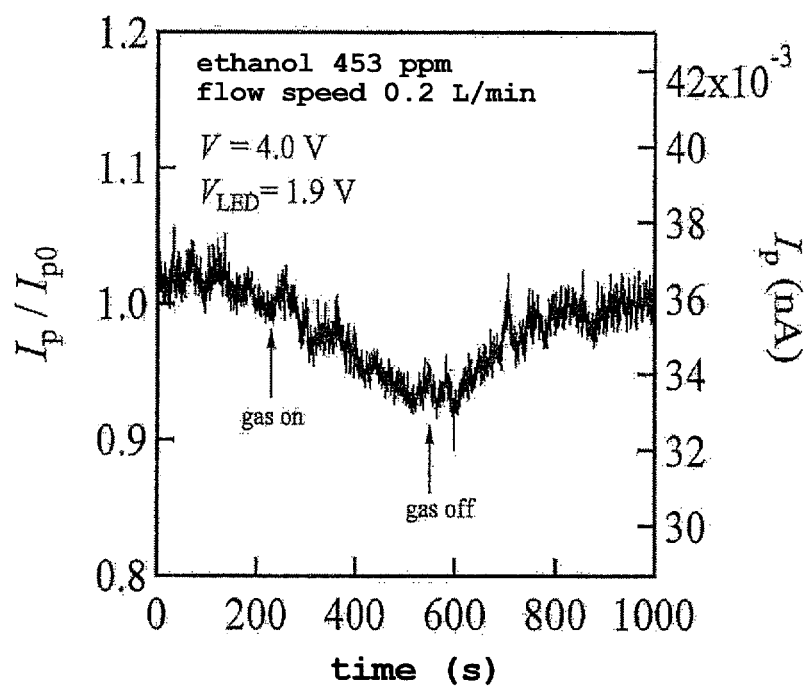
FIG. 17 shows the change in the electric current intensity ratio ($I_P/I_{P0}$)[$I_P=I_{ph}+I_b$] of photoelectric current value $I_P$ and photoelectric current value $I_{P0}$ before contact with gas, when ethanol gas (mixed gas of ethanol with ethanol concentration of 453 ppm and air) was contacted with SeNW in the wire electrode type gas sensor of FIG. 15.

FIG. 17 shows changes in the electric current intensity ratio between the photoelectric current value $I_P$ and the photoelectric current value $I_{P0}$ before contact with the gas ($I_P/I_{P0}$) [$I_P=I_{ph}+I_b$], when ethanol gas (mixed gas of ethanol and air with an ethanol concentration of 453 ppm, flow speed 0.2 L/min) was brought into contact with SeNW in the same manner.

Figure 18:
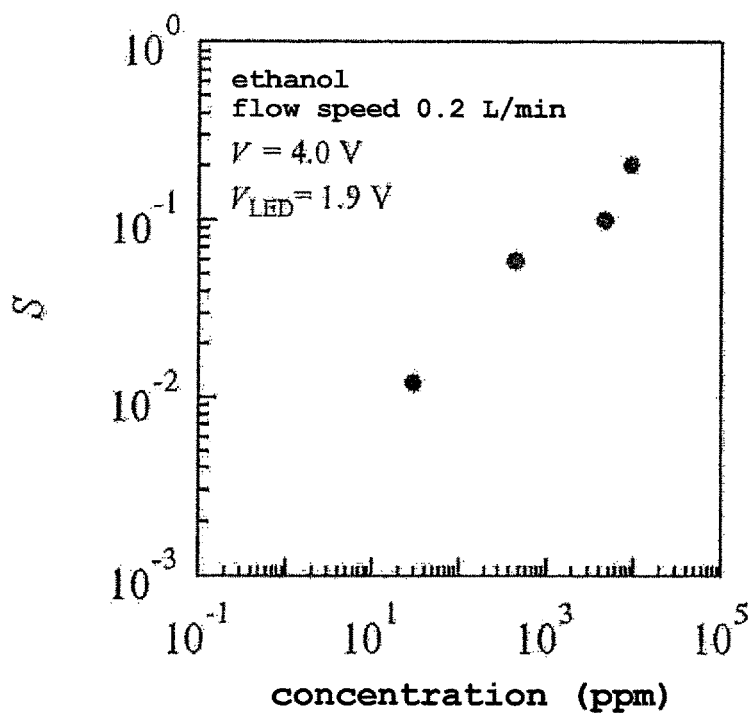
FIG. 18 shows the relationship between ethanol gas concentration and sensor sensitivity S in the wire electrode type gas sensor of FIG. 15.

From the results of FIGS. 16 and 17, it is clear that a gas sensor in which the photoelectric current value (electric current intensity ratio of photoelectric current value $I_P$ and photoelectric current value before contact with the gas $I_{P0}$ ($I_P/I_{P0}$) [$I_P=I_{ph}+I_b$]) changes along with the gas adsorption to the semiconductor nanowire can be easily realized even without using the parallel plate type counter electrodes, when semiconductor nanowires are arranged between the tips of two conductor wires to which voltage is applied and light is irradiated on the semiconductor nanowires. FIG. 18 shows the relationship between the ethanol gas concentration and sensitivity S when a mixed gas of ethanol gas and air with various ethanol gas concentrations was flown to SeNW at a flow speed of 0.2 L/min, from which it is clear that the gas sensor shows sensitivity S inherent to the concentration of the gas to be in contact with SeNW.

In a wire electrode type gas sensor, for example, a gas sensor can be constructed extremely easily by guiding two conductor wires such that their tip ends are opposed at a predetermined portion of a transparent insulating member (e.g., sealing resin of LED chip) containing a light source that emits light with energy not less than the vicinity of the bandgap of a semiconductor nanowire, and connecting the two conductor wires to a power supply.

4. Gas Sensor Array

Gas sensor array is a gas sensor array in which a plurality of the gas sensors of the present invention described above are arranged along the gas flow direction of the gas flow path.

The gas sensor array can be handled as a single device by providing a plurality of gas sensors and a gas flow path, through which the gas to be detected flows, on a single substrate.

Figure 19:
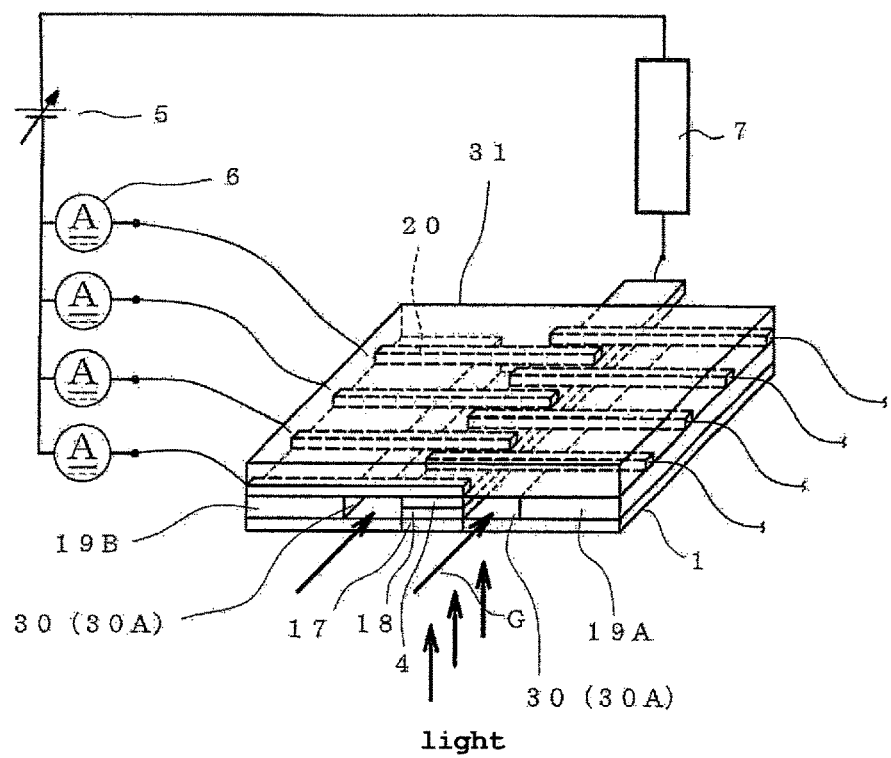
FIG. 19 is a perspective view of the first example of the gas sensor array of the present invention.

FIG. 19 is a perspective view schematically showing of one specific example of a gas sensor array as a single device.

A band-like glass plate extending in the second width direction is incorporated in the rectangular base 1 at substantial center in the first width direction, a first electrode 18 made of a band-like transparent electrode (e.g., ITO electrode) is formed on the surface of the glass plate 17, and a semiconductor nanowire 4 is disposed thereon. To prevent scattering of the wire and maintain the aggregate state of the wire, individual wires in the semiconductor nanowire 4 are bonded with a transparent resin binder such as PMMA (polymethyl methacrylate) and the like. Insulating wall portions 19A and 19B are disposed on both sides of the laminated structure of the first electrode 18/semiconductor nanowire 4, a gas flow path 30 is formed between the laminated structure of the first electrode 18/semiconductor nanowire 4 and the insulating wall portions 19A, 19B, and a plurality of narrow second electrodes 20 (e.g., copper electrode with gold plating on the surface on the semiconductor nanowire side) are arranged to extend from above the insulating wall portions 19A and 19B to the semiconductor nanowire 4 on the first electrode 18. Light from a light source (not shown) such as LED and the like is radiated on the semiconductor nanowire 4 through the glass plate 17 and the first electrode 18. In the Figure, reference numeral 31 is a cover for insulating between electrodes in a plurality of second electrodes 20 and closing up the upper part of the gas flow path 30, and reference numeral 30A is a gas inlet.

A sensor portion (gas sensor) is formed between the first electrode 18 and each of the electrodes of the plurality of second electrodes 20, and the number of the second electrodes 20 is the number of the sensor portions (gas sensors). That is, the first electrode 18 made of a band-like transparent electrode is a common electrode to be used as one electrode of the two opposed electrodes of each gas sensor of the plurality of gas sensors.

A circuit including a power source 5 and an ammeter 6 is formed for each sensor portion (gas sensor), and gas G is flown from the gas inlet 30A at one end of the gas flow path 30 to the gas flow path 30, and changes in photoelectric current caused by the contact of the gas with the semiconductor nanowire 4 is measured by each sensor portion (gas sensor).

In FIG. 19, while the number of the second electrodes 20 is 8 (i.e., 8 sensor portions (gas sensors)), the number is under limitation of space and, in the gas sensor array of the present invention, the number of the second electrodes 20 (i.e., number of sensor portions (gas sensors)) is freely set according to the gas measurement environment. While individual sensor portions (gas sensors) correspond to the gas sensors of FIG. 1, they may correspond to the gas sensors of FIG. 8.

The size of the rectangular base 1 is, for example, first width: 14.0 mm×second width: 12.0 mm, width of band-like glass plate is, for example, 1.0 mm, electrode width of the first electrode 18 composed of band-like transparent electrodes is, for example, 1.0 mm, and the amount of the semiconductor nanowire on the first electrode 18 per unit area is, for example, 13-50 μg/mm$^2$. In the second electrode 20, for example, electrode width is 0.1-0.2 mm, and distance between adjacent electrodes is 0.2-0.1 mm.

A performance example of this gas sensor array is shown below.

A gas sensor array having the constitution shown in FIG. 19, in which SeNW layer wherein SeNW (35 μg/mm$^2$) was bonded onto a band-like glass plate laminated with an ITO electrode (width 1.0 mm×length 12.0 mm) with PMMA, was formed, and 16 copper electrodes with gold plating (width: 0.2 mm, length: 7 mm) were arranged at 0.2 mm intervals on the surface of the SeNW layer side was produced. Two pieces of copper clad laminates were processed and disposed opposite to each other and used as base 1, insulating wall portions 19A and 19B, second electrode 20 and cover 31. The cross section of the two gas flow paths 30 (cross section orthogonal to the axis) was set to a rectangle having first width 0.95 mm×second width 0.12 mm (cross sectional area of 0.11 mm$^2$) and a rectangle having first width 1.0 mm×second width 0.12 mm (cross-sectional area of 0.12 mm$^2$).

The gas sensor nearest to the gas introduction port was set to be the first gas sensor (det 1), and the remaining 15 gas sensors were numbered in the order of an increasing clearance from the first gas sensor (det 1).

LED (Avago HLMP-C115, 637 nm) chip was operated at a voltage ($V_{LED}$) of 1.8 V with a stabilized power supply, and light from the LED chip was irradiated on SeNW at an irradiation intensity of 1.6 mW to photoexcite the SeNW to generate a photoelectric current.

The photoelectric current value of every gas sensor (any i$^{th}$ gas sensor (det i)) was measured under a constant voltage (30V) by a GPIB (General Purpose Interface Bus)-controlled digital multi meter (ADCMT 7461A), and the measurement data was constituted to be incorporated into a personal computer. GPIB control used was formed by a LabVIEW software manufactured by National Instrument. The minimum time decomposition ability was 0.05 sec. Data analysis was performed by Excell or Igor software.

The gas was developed by setting the tip of a cotton swab impregnated with an organic solvent at 1 mm from the gas sensor located most closely (the first gas sensor) to the gas introduction port into the gas flow path of the gas sensor array produced above.

For gas flow measurement, an organic solvent was injected with a syringe into a Tedlar Bag, diluted by injecting air, extracted from the bag by using a mini pump (MP-Σ30N manufactured by SHIBATA SCIENTIFIC TECHNOLOGY LTD.), and blown at an optional flow speed from 1 mm from a gas sensor located most closely (the first gas sensor) to the gas introduction port into the gas flow path of the gas sensor array produced in the above-mentioned Example.

Figure 20:
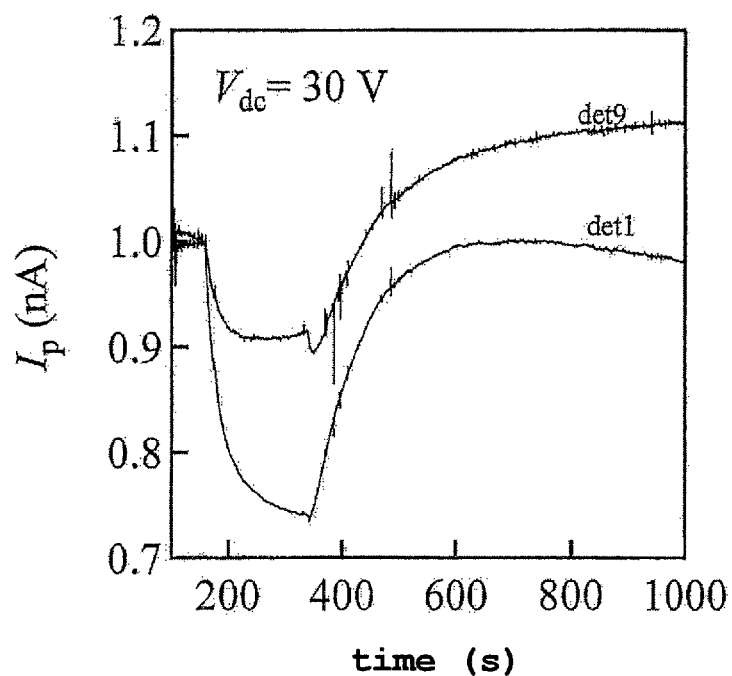
FIG. 20 shows one example of time-change spectrum of photoelectric current between the first gas sensor (det 1) and the ninth gas sensor (det 9), which are counted from the gas introduction port, when methanol gas was flown in the gas flow path in the gas sensor array of FIG. 19.
Figure 21:
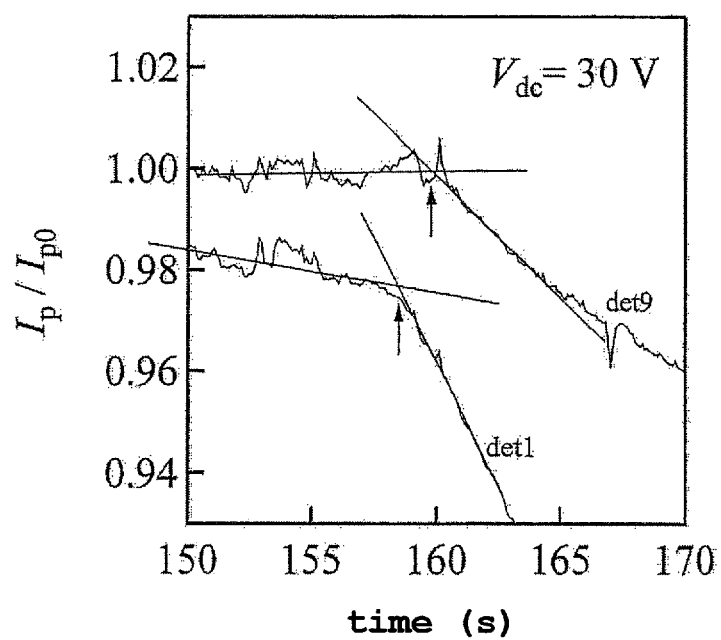
FIG. 21 shows one example of changes in the electric current intensity ratio ($I_P/I_{P0}$) [$I_P=I_{ph}+I_b$] between the first gas sensor (det 1) and the ninth gas sensor (det 9), which are counted from the gas introduction port, when methanol gas was flown in the gas flow path in the gas sensor array of FIG. 19.
Figure 22:
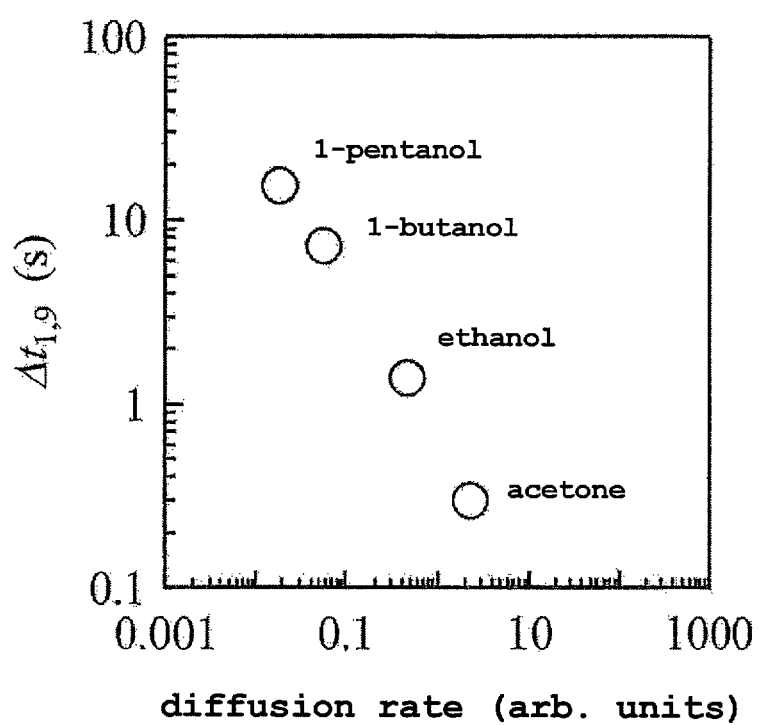
FIG. 22 shows the relationship between the first gas sensor (det 1) and the ninth gas sensor (det 9) in the delay time and the gas diffusion rate of the organic solvent: $\eta DP_0 M \ln[P_0/(P_0-P)]$, when 1-pentanol gas, 1-butanol gas, ethanol gas, and acetone gas were flown in the gas flow path in the gas sensor array of FIG. 19.

Examples of the measurement data obtained by performing the above operations are shown in FIGS. 20 to 22.

FIG. 20 shows time change spectrum of the photoelectric current of the first gas sensor (det 1) and the ninth gas sensor (det 9), which are counted from the gas introduction port, when DC voltage of 30 V was applied between the first electrode 18 and the second electrode 20 and methanol gas was flown, and FIG. 21 shows changes in the electric current intensity ratio of photoelectric current value $I_P$ and photoelectric current value before contact with the gas $I_{P0}$ ($I_P/I_{P0}$) [$I_P=I_{ph}+I_b$] in the first gas sensor (det 1) and the ninth gas sensor (det 9) at this time.

FIG. 22 shows the relationship between the first gas sensor (det 1) and the ninth gas sensor (det 9) in the delay time ($\Delta t_{1,9}$) (s) and gas diffusion rate [$\eta D P_0 M \ln[P_0/(P_0-P)]$] (gs$^{-1}$)], when 1-pentanol gas, 1-butanol gas, ethanol gas, and acetone gas were flown in the gas flow path. As used herein, $\eta$ is proportionality constant, D is gas diffusion coefficient, $P_0$ is standard pressure, M is molecular weight, and P is gas vapor pressure.

In the gas sensor array (gas sensor array) of the present invention, the electric output values (delay time, peak time, spectrum shape etc.) based on the time-change spectrum of photoelectric current value (electric current intensity ratio of photoelectric current value $I_P$ and photoelectric current value before contact with the gas $I_{P0}$ ($I_P/I_{P0}$) [$I_P=I_{ph}+I_b$]) that occurs in each gas sensor show specific values for each gas, when the gas to be analyzed is flown in a gas flow path while applying a constant voltage to plural gas sensors. Therefore, an automatic gas analysis system can be constituted by forming a gas detection map of each gas in advance, which correlates such values with the property values of the gas, as a database, and additionally setting a calculation part that specifies gas type, component ratio of a mixed gas or gas component of a mixed gas by utilizing the database, on a gas sensor array.

One embodiment of the determination method of the gas type, component ratio of the mixed gas and the like by an automatic measurement program for an automatic gas analysis system is shown below.

[I] Determination of Reaction Start Time of Each Sensor by Contact with Gas in Gas Sensor Array, and Measurement of Gas Type and Mixed Gas Component Ratio and the Like 1. Determination of Initial Photoelectric Current Value $I_0$ Before Contact with Gas:

To reduce time variation due to the noise of the photoelectric current that flows in the $k^{th}$ sensor det k before contact with a gas, an average time $<I_{k,0}>$ of the photoelectric current value that flows in the sensor is determined.

2. Determination of the Presence or Absence of Decrease in Photoelectric Current Value Due to Contact with Gas:

The kth sensor det k reacts on contact with a gas, and the photoelectric current value $I_k$ that flows in this sensor starts to decrease from $<I_{k,0}>$. At this time, the electric current value $I_{k,j}(t_{k,j})$ at measurement time $t_{k,j}$ is measured, $[I_{k,j}(t_{k,j})-<I_{k,0}>]$ is calculated, plus and minus is determined, and the number of minus $n_k$ is determined. This value is compared with the upper limit value $N_k$ of the number of minus relative to the kth sensor det k and whether it reaches $N_k$ is determined.

3. Determination of Reaction Start Time by Contact with Gas:

In the kth sensor det k, when $N_k$ in 2. was judged to have been reached, a time period that went back from the time $t_{k,j,N}$ when $N_k$ in 2. was reached ($t_{k,j,N}-N_k \Delta t$) [$\Delta t$ is data obtainment time interval (measurement decomposition ability of apparatus)] is $t_{k,on}$.

4. Calculation of Difference $\Delta t_{1,k}$ in Reaction Start Time:

Using the value of reaction start time $t_{k,on}$ on of each sensor det k determined in 3., a difference in the reaction start time ($\Delta t_{1,k}=t_{k,on}-t_{1,on}$) from the $t_{1,on}$ value of the first sensor det 1 is calculated.

5. Determination of Gas Type, Mixed Gas Component Ratio and the Like:

The gas type, mixed gas component ratio and the like can be determined by comparing the value of $\Delta t_{1,k}$ with the data obtained previously.

Figure 23:
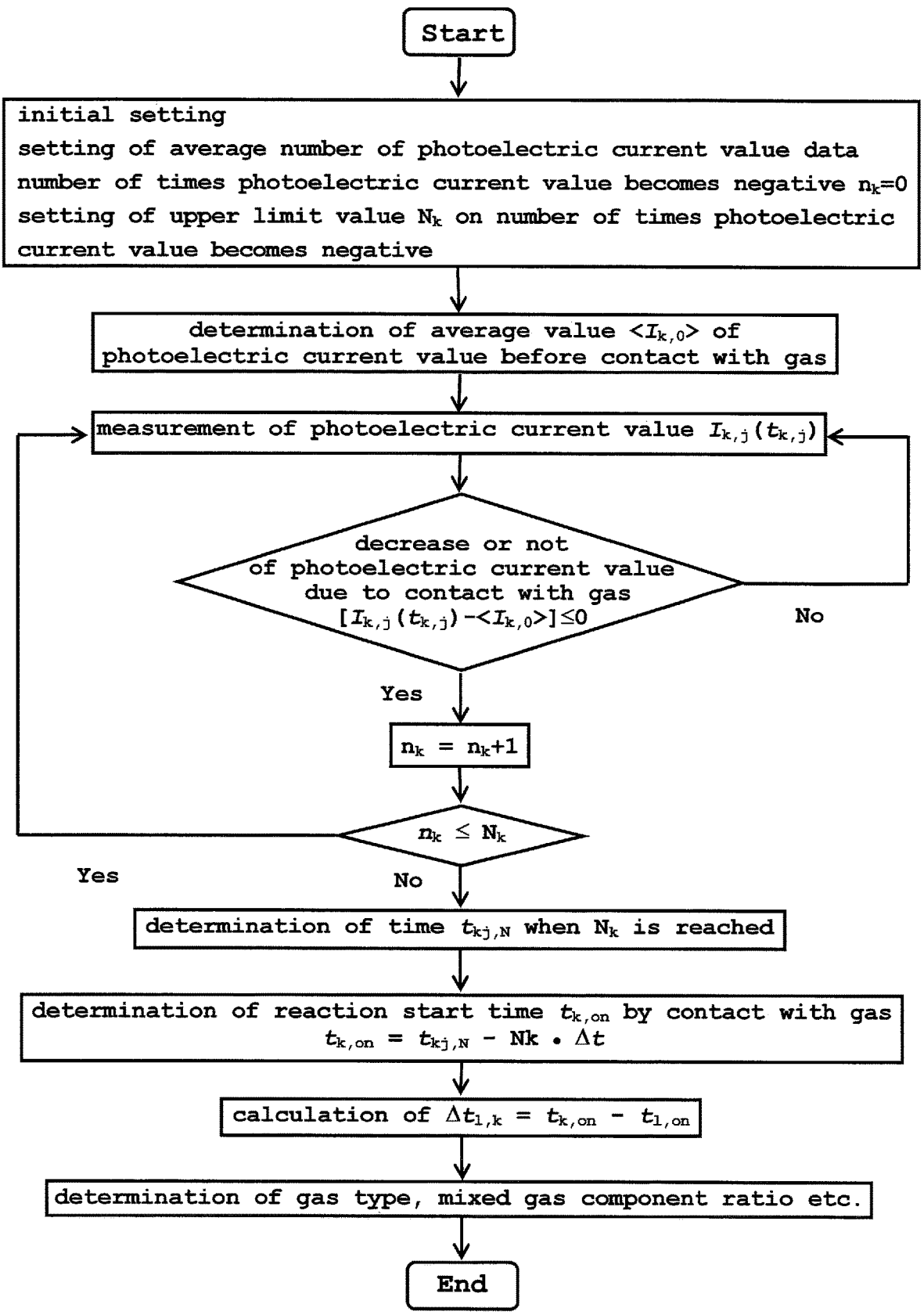
FIG. 23 is a flow chart showing an exemplary program relating to the determination of reaction start time of each sensor and the measurement of gas type, mixed gas component ratio and the like in the automatic gas analysis system using the gas sensor array of the present invention.

A flow chart is shown in FIG. 23.

[II] Measurement of Sensor Sensitivity S

The determination of the gas type can be performed more accurately by, for example, combining a program for determination by automatic measurement of sensor sensitivity S by the simple type sensor described in JP-B-5120904 by the present inventors. The following shows the program thereof. For the measurement, the first gas sensor (det 1) of a gas sensor array is used. In the following program, the measurement was performed at each sensor of a gas sensor.

1. Determination of Initial Photoelectric Current Value $I_0$ Before Contact with Gas:

To reduce time variation due to the noise of the photoelectric current that flows in the kth sensor det k before contact with a gas, an average time $<I_{k,0}>$ of the photoelectric current value that flows in the sensor is determined.

2. Determination of the Presence or Absence of Decrease in Photoelectric Current Value Due to Contact with Gas:

The kth sensor det k reacts on contact with a gas, and the photoelectric current value $I_k$ that flows in this sensor starts to decrease from $<I_{k,0}>$. At this time, the data of the photoelectric current value $I_{k,j}(t_{k,j})$ at a measurement time $t_{k,j}$ is obtained by performing an average treatment at a predetermined time interval. A difference in the photoelectric current value between measurement times $t_{k,j}$ and $t_{k,j+1}$, $\Delta I_{k,j,j+1}=<I_{k,j+1}(t_{k,j+1})>-<I_{k,j}(t_{k,j})>$, is calculated, and plus and minus is determined.

3. Determination of Minimum Value of Photoelectric Current Value of the Kth Sensor Det k Due to Contact with Gas:

The photoelectric current value $<I_{k,m}(t_{k,m})>$ at the time $t_{k,m}$ when the photoelectric current value of the kth sensor det k changes from minus to plus by the determination in 2. is the minimum value.

4. Calculation of Sensor Sensitivity:

The sensor sensitivity S of the kth sensor det k can be obtained by $[<I_{k,0}>-<I_{k,m}(t_{k,m})>]/<I_{k,0}>$.

5. Determination of Gas Type:

The gas type can be determined by comparing the S value with the data obtained previously.

Figure 24:
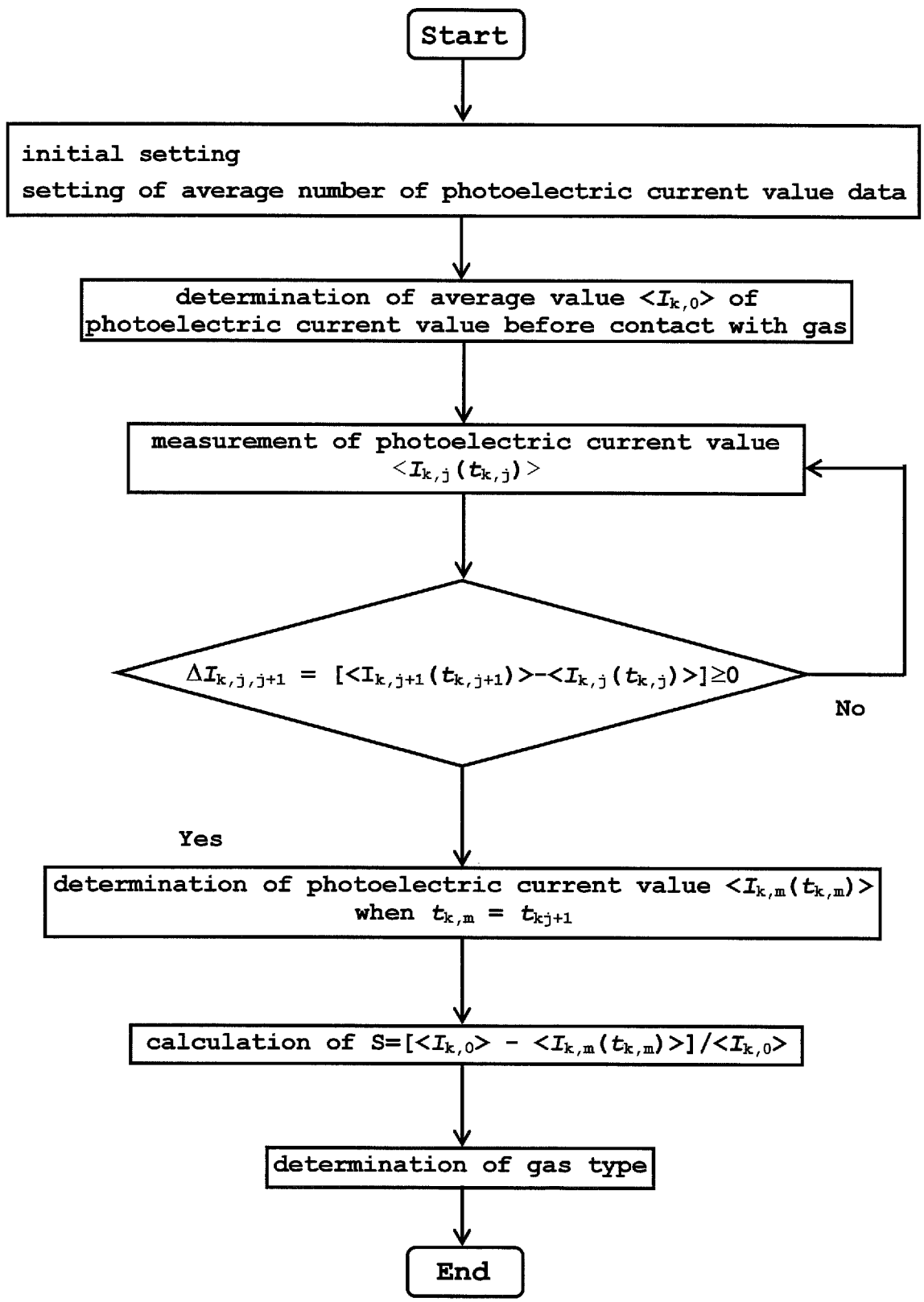
FIG. 24 is a flow chart showing an exemplary program relating to the measurement of sensor sensitivity S in the automatic gas analysis system using the gas sensor array of the present invention.

A flow chart is shown in FIG. 24.

Measurement of the light intensity of LED and laser in the performance example of the aforementioned each type of the gas sensor and Experimental Examples described below in the present specification was performed by using an optical measurement system (LABMASTER) manufactured by Coherent Co., Ltd. and its light detection head (LM-2, CW measurement, measurable range 10 nW to 5 W, resolution 1 nW). That is, the distance between the light source (LED, laser) and the light detection head was made substantially the same as the distance (irradiation distance) to the semiconductor nanowire (SeNW) in the gas sensor from the light source (LED, laser), and the light intensity of the light source was measured. Therefore, the light intensity of the LED and laser corresponds to the irradiation intensity of the light hitting the semiconductor nanowire. The flare angle of the LED used (Avago HLMP-C 115, 637 nm) was 15 degrees; the flare angle of the laser pointer (manufactured by Sakura Crepes Co., RX-4, 1 mW type, wavelength: 649 nm, photon energy ($E_{ph}$): 1.91 eV) was 0.1 degree and the beam diameter thereof was 0.6 mm; and the flare angle of He—Ne laser (manufactured by NEC, GLG5370, 3 mW type, wavelength: 633 nm, photon energy ($E_{ph}$): 1.96 eV) was 1.23 mrad and the beam diameter thereof was 0.65 mm. Therefore, the light intensity of the light source (LED, laser) itself is measured by the light detection head. Since the light irradiated from each light source to the sensor was measured with the light as it was without using a lens and the like, conversion into power density is also possible under the above-mentioned conditions. Here, the output result from the light detection head was directly used as the light intensity.

EXPERIMENTAL EXAMPLES

Experimental Examples verifying the relationship between the electric field intensity and the sensitivity between counter electrodes, the relationship between the light irradiation intensity on the semiconductor nanowire and sensitivity, and the like in the gas sensor of the present invention are shown below.

Experimental Example 1

Figure 25:
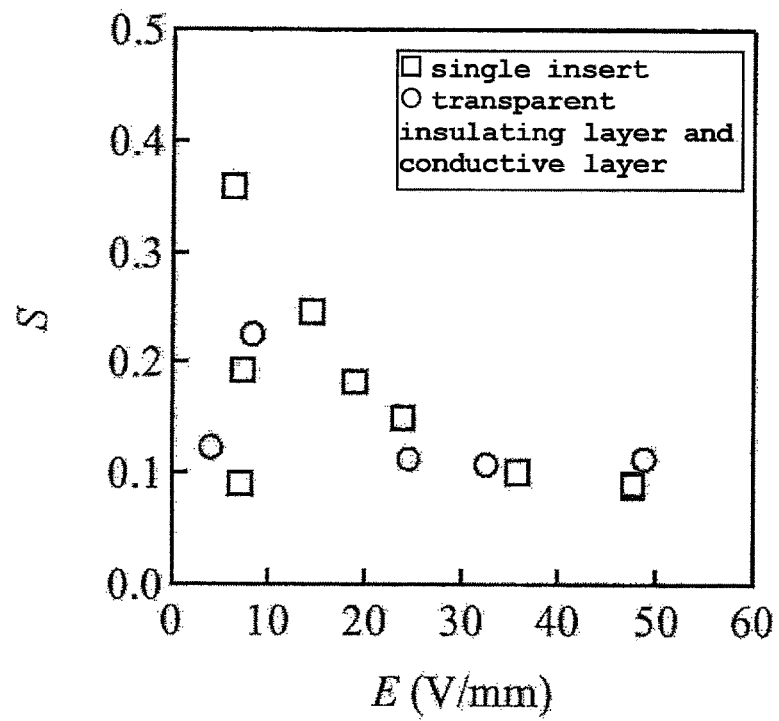
FIG. 25 shows the relationship between electric field intensity E between counter electrodes and gas sensor sensitivity S, in the second example gas sensor (FIG. 7) and the fourth example gas sensor (FIG. 9) of the light-transmissive electrode type gas sensor.

In the gas sensor of the second example (FIG. 7) and the gas sensor of the fourth example (FIG. 9) of the light-transmissive electrode type gas sensor, the sensitivity S of the gas sensor was measured by variously changing the electric field intensity E between counter electrodes. FIG. 25 shows the results thereof. In the gas sensor of the second example, only the semiconductor nanowire (layer) was interposed between the counter electrodes and insulating layer and conductive layer were not inserted. In the gas sensor of the fourth example, a transparent insulating layer and a conductive layer were inserted between the counter electrodes. Therefore, "single insert" in the Figure refers to the gas sensor of the second example, and "transparent insulating layer and conductive layer" refers to the gas sensor of the fourth example.

From FIG. 25, it is clear that the electric field intensity E between counter electrodes markedly influences sensor sensitivity S. That is, when the electric field intensity E between counter electrodes is high (high voltage is applied to counter electrodes), while a large amount of photoelectric current flows in the semiconductor nanowire, carriers responsible for the electric current (photoelectric current carriers) cannot be captured efficiently by dipoles that the gas has, since the speed of the carrier is high (that is, photoelectric current carrier near the surface of the semiconductor nanowire cannot efficiently encounter and be neutralized by electrons (positive holes) injected from the gas). The sensitivity of the sensor is determined by the ratio of photocarriers captured by the electrons (positive holes) injected from the gas. Even if a large amount of photoelectric current flows, the capture efficiency of the photocarrier deteriorates and the sensitivity (S value) of the sensor decreases due to the influence of an increase in the electric field intensity E. Therefore, it is clear that, in the gas sensor of the present invention, it is important for sensor sensitivity S to optimize the electric field intensity E between the counter electrodes, and a sensor constitution in which the electric field intensity E between the counter electrodes is 3-34 V/mm (preferably 6-20 V/mm) in absolute value is preferably adopted.

The constitution of the sensor subjected to the experiment is as follows.

overlap area of counter electrodes: 0.5×0.5 mm²
semiconductor nanowire: SeNW (1.56 mg/mm³)
distance between electrodes of counter electrodes: 0.05 to 0.30 mm
light source: LED (Avago HLMP-C115, 637 nm) 3.1 mW
gas to be detected: ethanol gas (gas was generated by setting the tip of a cotton swab impregnated with ethanol at a position 1 mm away from the gas sensor.
Note) The above sensor constitution is common to the gas sensor of the second example and the gas sensor of the fourth example.
transparent insulating layer: PMMA layer (thickness: 0.75-1.66 μm)
conductive layer:carbon tape (thickness: 0.16 mm)

The electric field intensity between the counter electrodes was adjusted by preparing elements having different distance between electrodes of the counter electrodes and controlling the applied voltage.

Experimental Example 2

Figure 26:
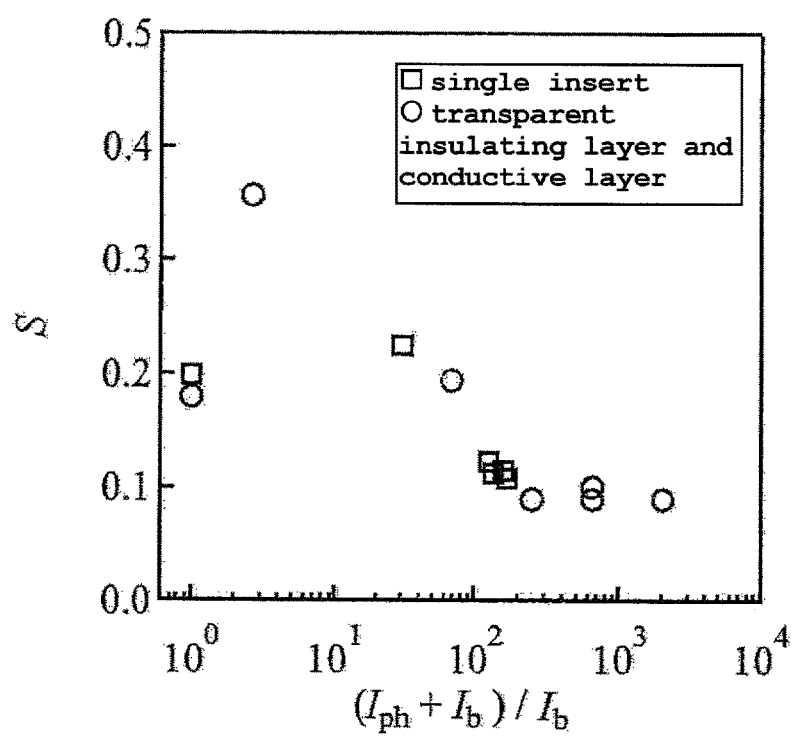
FIG. 26 shows the relationship between the ratio of the measured electric current value $I_{ph}+I_b$ of photoelectric current and base current value $I_b$ ($I_{ph}+I_b$)/$I_b$, and S value of ethanol gas, in the second example gas sensor (FIG. 7) and the fourth example gas sensor (FIG. 9) of the light-transmissive electrode type gas sensor.

In the gas sensor of the second example (FIG. 7) and the gas sensor of the fourth example (FIG. 9) of the light-transmissive electrode type gas sensor, the value of the ratio of the measured electric current value $I_{ph}+I_b$ of the photoelectric current and the base current $I_b$ $(I_{ph}+I_b)/I_b$ was adjusted by changing the light intensity of LED (Avago HLMP-C115, 637 nm) and applied voltage V, and the S value of the ethanol gas was measured. FIG. 26 shows the results thereof.

From FIG. 26, it is clear that a sensor constitution wherein the ratio of the measured electric current value ($I_{ph}+I_b$) by light irradiation and the base current value ($I_b$) (($I_{ph}+I_b)/I_b$) is 1.5-70 (preferably 1.8-10) is preferable for achieving a large level of sensor sensitivity S.

The experiment conditions were as described below.

The constitution of the sensor subjected to the experiment is as follows.

overlap area of counter electrodes: 0.5×0.5 mm²
semiconductor nanowire: SeNW (1.56 mg/mm³)
distance between electrodes of counter electrodes: 0.05 to 0.30 mm
light source: LED (Avago HLMP-C115, 637 nm) 0-3.2 mW
applied voltage: 0.5-1.0V gas to be detected: ethanol gas (gas was generated by setting the tip of a cotton swab impregnated with ethanol at a position 1 mm away from the gas sensor.

Experimental Example 3

Figure 27:
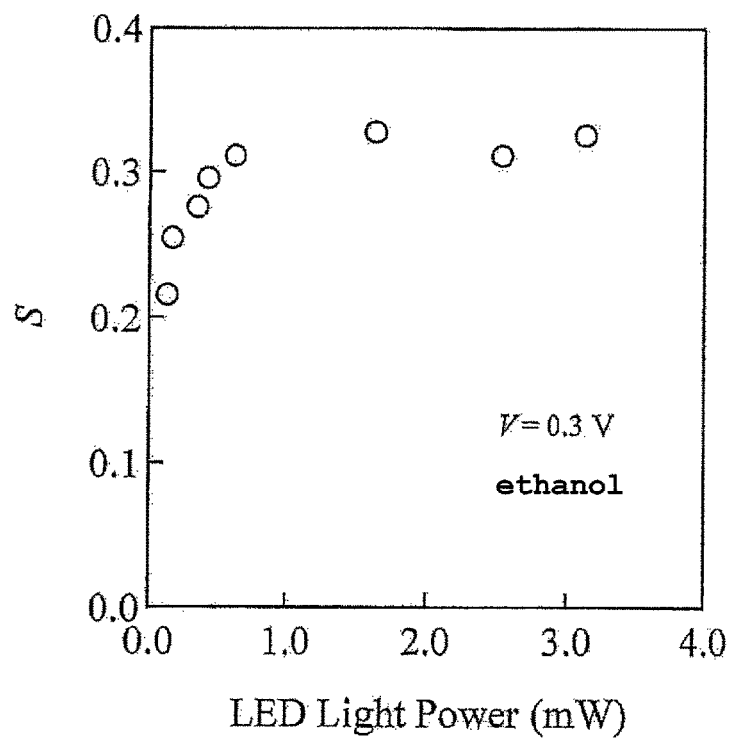
FIG. 27 shows the relationship between the light intensity of a light source (LED) and S value of ethanol gas, in the second example gas sensor (FIG. 7) of the light-transmissive electrode type gas sensor.

In the gas sensor of the second example (FIG. 7) of the light-transmissive electrode type gas sensor, the S value of the ethanol gas was measured by variously changing the light intensity of LED (Avago HLMP-C115, 637 nm). FIG. 27 shows the results thereof.

The experiment conditions were as described below.
overlap area of counter electrodes: 0.5×0.5 mm$^2$ semiconductor nanowire: SeNW (1.56 mg/mm$^3$)
distance between electrodes of counter electrodes: 0.021 mm light source: LED (Avago HLMP-C115, 637 nm) 0-3.2 mW applied voltage: 0.3V
gas to be detected: ethanol gas (gas was generated by setting the tip of a cotton swab impregnated with ethanol at a position 1 mm away from the gas sensor.

When photoelectric current $I_{ph}$=0, the measured electric current value of the photoelectric current $I_{ph}+I_b$ becomes $I_b$, and corresponds to the S value in the gas reaction at the base current, that is, the gas sensor without conventional light irradiation (gas sensor of patent document 1).

From FIG. 26, it is clear that, in the measurement while the photoelectric current $I_{ph}$ is flowing, a small amount of photoelectric current $I_{ph}$ (that is, low voltage application=low electric field intensity) causes an increase in the S value (that is, improvement of sensor sensitivity) as compared to photoelectric current $I_{ph}$=0 (conventional sensor with only base current $I_b$).

In FIG. 26, it is considered from $(I_{ph}+I_b)/I_b$=3 that $I_{ph}$=about 2·$I_b$ is the optimal conditions of S. When $(I_{ph}+I_b)/I_b$ is near 10$^3$, the value of S is smaller than when $(I_{ph}+I_b)/I_b$ is 1. This is because high photoelectric current obtained by application of high voltage cannot capture the generated photocarriers.

The photoelectric current density J is expressed by J=qnμE, wherein q is electric charge (electron or positive hole), n is carrier density generated by photoexcitation, μ is carrier mobility, and E is electric field intensity. The carrier density n increases as the light excitation intensity increases, and the electric field intensity E=V/d increases as the applied voltage V increases and increases as the sensor gap d decreases. On the other hand, $I_{ph}+I_b$ is proportional to J. It is considered, therefore, that the optimum optical carrier density n can be obtained by adjusting the gaps (sensor gap) d and V of the counter electrodes to achieve the optimal electric field intensity E and adjusting the irradiation intensity of the light to SeNW to $I_{ph}$=2·$I_b$. However, in the actual measurement results based on the light intensity of LED (FIG. 27), the S value was saturated with a relatively weak light. It is considered that saturation due to photoexcitation of carrier density n is related to the lifetime thereof.

It was found from these results that a wide range can be set for the irradiation intensity of light on the semiconductor nanowire, and therefore, it is important to optimize the electric field strength between counter electrodes.

In addition, since the intensity of the electric field between counter electrodes decreases and the base current $I_b$ can be reduced by inserting an insulator (transparent insulating layer) into the gap (sensor gap) of counter electrodes, the power of the irradiation light to the semiconductor nanowire can be lowered.

Figure 28:
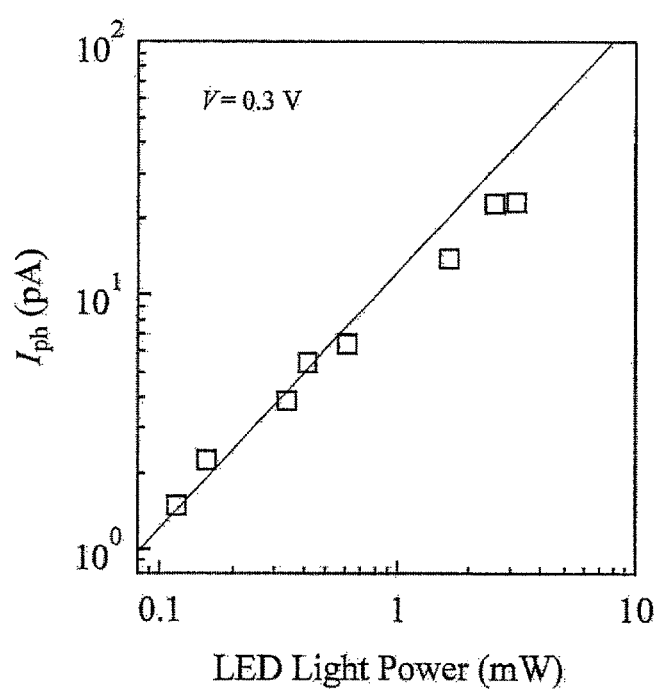
FIG. 28 shows the relationship between the light intensity of a light source (LED) and the photoelectric current $I_{ph}$ flowing in the element (SeNW), in the second example gas sensor (FIG. 7) of the light-transmissive electrode type gas sensor.

In FIG. 28, only the photoelectric current $I_{ph}$ of the element was determined by subtracting the base current $I_b$ from the photoelectric current $I_{ph}+I_b$ before contact with the gas, which was obtained in the experiment of Experimental Example 3, and the relationship with the light intensity of LED was investigated.

The experiment conditions were as described below.
overlap area of counter electrodes: 0.5×0.5 mm$^2$
semiconductor nanowire: SeNW (1.56 mg/mm$^3$)
distance between electrodes of counter electrodes: 0.021 mm
light source: LED (Avago HLMP-C115, 637 nm) 0-3.2 mW
applied voltage: 0.3V In FIG. 28, $I_{ph}$ is increasing mostly in proportion to the light intensity of LED, and the S value in FIG. 27 is saturated at not less than 0.6 mW. This suggests that the same measured value can be obtained at not less than 0.6 mW, even if the intensity of light slightly fluctuates. It was suggested that the gas sensor of the present invention can also be used by irradiation of light with varying light intensity, such as natural light, on the semiconductor nanowires.

INDUSTRIAL APPLICABILITY

The gas sensor of the present invention utilizing a photoelectric current can perform gas detection by efficient gas contact. Therefore, a sensor with high sensitivity and high responsiveness can be realized while using a smaller amount of semiconductor nanowires than a gas sensor using a conventional semiconductor nanowire (SeNW). As a gas type to be detected, it can detect organic gas, carbon dioxide gas, and the like with high sensitivity. Since the gas sensor is compact, it can be incorporated into various integrated circuit chips in combination with LED, and it is expected to be usable for small equipment such as sensors for health monitoring. In addition, a sensor with an array structure can be an ultra small portable gas component analyzer that replaces gas chromatography.

This application is based on a patent application No. 2014-139118 filed in Japan, the contents of which are incorporated in full herein.

EXPLANATION OF SYMBOLS 1 base
2, 3 counter electrodes
4 semiconductor nanowire
5 power supply
6 ammeter
7 protective resistor for circuit protection in short circuit
8 transparent insulating substrate
9 transparent electrode
21 gold thin film layer
22 copper layer

The invention claimed is:
1. A gas sensor comprising counter electrodes and a selenium nanowire disposed between the counter electrodes, which sensor shows a change in a photoelectric current $I_{ph}$ associated with adsorption of a gas to the selenium nanowire,
wherein the photoelectric current $I_{ph}$ is generated by irradiation of light on the selenium nanowire with a voltage applied to the counter electrodes,
wherein the selenium nanowire is in a state where light can be irradiated thereon, and
wherein each of the counter electrodes has an inner surface, and an insulating layer is provided on the inner surface of one of the counter electrodes.

2. The gas sensor according to claim 1, wherein respective wires in the selenium nanowire are bonded with a transparent insulating resin binder.

3. The gas sensor according to claim 1, wherein at least one of the counter electrodes is a transparent electrode.

4. The gas sensor according to claim 3, wherein the transparent electrode has an inner surface, and the transparent electrode comprises a transparent insulating layer, as the insulating layer, provided on the inner surface thereof.

5. The gas sensor according to claim 3, wherein one of the counter electrodes is a transparent electrode and the insulating layer is provided on the inner surface of the transparent electrode, and the other counter electrode comprises a conductive layer provided on the inner surface of the other counter electrode.

6. The gas sensor according to claim 3, wherein the at least one transparent electrode has an outside surface, the selenium wire has an energy near a bandgap of the selenium wire, and the gas sensor has a light source arranged to irradiate light on the outside surface of the transparent electrode that emits light with energy which is not less than the energy near the bandgap of the selenium nanowire.

7. The gas sensor according to claim 1, wherein a conductive layer is provided on the inner surface of the other counter electrode.

8. The gas sensor according to claim 1, wherein the change in the electric current is a change in the electric current intensity.

9. The gas sensor according to claim 1, wherein the counter electrodes applied with a voltage have an electric field intensity (absolute value) of 3-34 V/mm.

10. A gas sensor comprising counter electrodes and a selenium nanowire disposed between the counter electrodes, which sensor shows a change in a photoelectric current $I_{ph}$ associated with adsorption of a gas to the selenium nanowire,
wherein the photoelectric current $I_{ph}$ is generated by irradiation of light on the selenium nanowire with a voltage applied to the counter electrodes,
wherein the selenium nanowire is in a state where light can be irradiated thereon,
wherein the distal ends of two conductor wires face each other and the distal ends of the two conductor wires form the counter electrodes, and the selenium nanowires are disposed between the tips of the two conductor wires, and
wherein an insulating layer is provided on the tip of one of the two conductor wires.

11. The gas sensor according to claim 10, wherein the selenium wire has an energy near a bandgap of the selenium wire, and the tips of the two conductor wires are led to face each other at a predetermined portion of a transparent insulating member containing a light source that emits light having energy which is not less than the energy near the bandgap of the selenium nanowire.

12. A gas sensor array comprising a plurality of gas sensors, which are arranged along a gas flow direction of a gas flow path through which a gas to be detected flows,
wherein each of the plurality of gas sensors comprises counter electrodes and a selenium nanowire disposed between the counter electrodes, which sensors show a change in a photoelectric current $I_{ph}$ associated with adsorption of a gas to the selenium nanowire,
wherein the photoelectric current $I_{ph}$ is generated by irradiation of light on the selenium nanowire with a voltage applied to the counter electrodes,
wherein the selenium nanowire is in a state where light can be irradiated thereon, and
wherein each of the counter electrodes has an inner surface, and an insulating layer is provided on the inner surface of one of the counter electrodes.

13. The gas sensor array according to claim 12, comprising a single electrode arranged such that its axis is parallel to the gas flow direction of the gas flow path through which the gas to be detected flows, wherein the single electrode is a common electrode used as one of two opposing electrodes of individual gas sensors in the plurality of gas sensors.

14. The gas sensor array according to claim 13, wherein the single electrode is a transparent electrode.

15. The gas sensor array according to claim 12, wherein the gas to be detected that flows in the gas flow path comes into contact, under a constant voltage, with selenium nanowires of plural gas sensors to generate time-change spectrum of photoelectric current intensity in each gas sensor, and a delay time between different sensors is detected.

16. A gas analysis system comprising the gas sensor array according to claim 12, and a calculation part for specifying a gas type, specifying a component ratio of a mixed gas or specifying gas components of a mixed gas, which is based on comparison results of an electric output value based on a change in photoelectric current that occurs in each gas sensor when a gas to be detected is flown in a gas flow path while applying a constant voltage to plural gas sensors in the gas sensor array, and numerical values preserved in a database.

17. The gas sensor according to claim 1, wherein the gas sensor has a ratio {(photoelectric current $I_{ph}$+base current $I_b$)/base current $I_b$} of 1.5-70, wherein the base current $I_b$ is an electric current that flows without irradiating light on the selenium nanowire with a voltage applied to the counter electrodes.

18. The gas sensor according to claim 17, wherein the ratio {(photoelectric current $I_{ph}$+base current $I_b$)/base current $I_b$} is 1.8-10.

* * * * *